United States Patent [19]
Schroeder et al.

[11] Patent Number: 5,353,796
[45] Date of Patent: Oct. 11, 1994

[54] NON-INVASIVE DEVICE AND METHOD FOR GRADING MEAT

[75] Inventors: Aubrey L. Schroeder, Greenfield; James T. Whitehead, Carmel, both of Ind.; Thomas E. Michel, Centerville; David L. Petricola, Dayton, both of Ohio

[73] Assignee: Eli Lilly and Company, Indianapolis, Ind.

[21] Appl. No.: 722,914

[22] Filed: Jun. 28, 1991

[51] Int. Cl.$^5$ ............................................... A61B 8/00
[52] U.S. Cl. ................................. 128/660.01; 73/602; 128/661.03
[58] Field of Search ....................... 128/660.01, 660.06, 128/660.07, 661.03, 660.09; 73/602, 644

[56] References Cited
U.S. PATENT DOCUMENTS

| | | | |
|---|---|---|---|
| 3,496,764 | 2/1970 | Stouffer | 73/644 X |
| 3,603,303 | 9/1971 | Stouffer | 128/660.01 |
| 3,722,263 | 3/1973 | Hautaniemi et al. | 73/622 |
| 4,094,420 | 7/1978 | Stouffer et al. | 73/629 |
| 4,359,055 | 11/1982 | Carlson | 73/631 X |
| 4,359,056 | 11/1982 | Carlson | 73/631 X |
| 4,785,817 | 11/1988 | Stouffer | 128/660.07 |
| 5,079,951 | 1/1992 | Raymond et al. | 128/660.07 X |
| 5,140,988 | 8/1992 | Stouffer et al. | 128/660.01 |

FOREIGN PATENT DOCUMENTS

| | | | |
|---|---|---|---|
| 0337661 | 10/1989 | European Pat. Off. | |
| 2007364 | 5/1979 | United Kingdom | 128/660.1 |
| 2213263 | 12/1987 | United Kingdom | 128/660.01 |

OTHER PUBLICATIONS

R. J. W. Lake, *Ultrasonics in Meat Quality*.
Rouse et al. "The Use of Real-time Ultrasound to Measure Marbling in Live Steers and Beef Carcasses", J. Animal Sci., vol. 63, Suppl. pp. 398-399.
H. A. Recio et al., "Use of Real-Time Ultrasound For Predicting Beef Carcass Cutability", J. of Animal Sci., vol. 63, Supp 1, pp. 260-261.
M. F. Miller et al., "Evaluation of Live and Carcass Techniques for Predicting Beef Carcass Composition," vol. 63, Suppl. 1, p. 261.
C. D. Bacon et al., "Prediction of Pork Carcass Composition by the Pork Loin 3-6 Rib Section", J. of Animal Sci, vol. 63, Supp. 1, p. 259.
Kreider et al. "Comparison of Ultrasound Imaging of Market-weight Pigs with Conventional Methods of Carcass Evaluation," J. of Animal Sci,, vol. 63 pp. 33-34.
May et al., "Ultrasound Atenuation Coefficient Assessment in Bovine Muscle", J. Animal Sci., vol. 65, Suppl. 1, p. 281.

(List continued on next page.)

Primary Examiner—Francis Jaworski
Attorney, Agent, or Firm—Woodard, Emhardt, Naughton, Moriarty & McNett

[57] ABSTRACT

A non-invasive apparatus and method for measuring fat thickness or content and muscle depth or area parameters grading meat and animals are disclosed. The device includes an ultrasonic transducer and analyzer device which provides A scan information in digitized form. A separate controller moves the ultrasonic transducer along a predetermined path adjacent an animal or carcass while A scans are obtained at predetermined locations along the path. The A scans are digitized and analyzed to determine the tissue interface boundaries. Equations are implemented to determine the area of the longissimus muscle and fat tissue thicknesses and a lean content rating for the animal may be determined therefrom. Modeling techniques are also used to estimate certain portions of the area of the longissimus muscle of the animal or carcass based upon data gathered during the ultrasound scanning of the carcass. Scanning of the ham area and round (beef) using the ultrasonic scanner is also suggested to add increased reliability to the data obtained from scanning the rib or loin eye area when used in conjunction therewith in a leanness prediction equation.

26 Claims, 23 Drawing Sheets

OTHER PUBLICATIONS

Properties of Mammilain Tissues II" J. Acoust. Soc. Am., vol. 68, No. 1 (1980).

Anderson et al. *Ultrasonic Prediction of Swine Carcass Composition*, S. Dakota St. University, Brookings, Publication No. 845.

Haumschile et al., "An Ultrasonic Brag Scattering Technique for the Quantitative Characterization of Marbling in Beef", Ultrasonics, pp. 226–233, (Sep. 1983).

Miles et al. "A Note on the Velocity of Ultrasound in Living Tissue," Anim. Prod. vol. 18, pp. 93–96 (1974).

Kanis et al., "Prediction of Lean Parts and Carcass Price from Ultrasonic Backfat Measurements in Live Pigs," Livestock Prod. Sci. vol. 14 pp. 55–64 (1986).

Lenhert et al. "The Design and Testing of an Automated Beef Grader", Paper No. 85-3035 (1985 meeting of Am. Soc. of Agri. Engineers).

Isler, "Ultrasonic Prediction of Lean Cut Percent in Swine," J. Anim. Sci. vol. 27 pp. 377–382 (1968).

McMillan et al., "Comparisons of Ultrasonic Imaging and Conventional Measurements of Live Swine and Pork Carcass Fat Thickness and Muscling", J. Ani. Sci. vol. 19 pp. 79–80 (1960).

Price et al., "Application of Ultrasonic Reflection Techniques and Evaluating Fatness and Leanness in Pigs," J. of Animal Sci., vol. 19, pp. 381 (1960).

Price et al., "Measurement of the Cross–Sectional Area of Loin Muscle in Live Swine by Ultrasonic Reflections", J. of Animal Sci. pp. 786–789.

Stouffer et al., "Development and Application of Ultrasonic Methods for Measuring Fat Thickness in Rib Eye Area in Cattle and Hogs," J. of Animal Sci. vol. 25, p. 759.

Davis et al. "A Comparison of Ultrasonic Estimates of Rib–Eye Area and Fat Thickness in Cattle," J. of Animal Sci., vol. 65, Suppl. 1 pp. 1087–1090.

Parrett et al. "The Use of Technicare Real–time Linear Array Ultrasound Equipment for Fat Determination in Beef Cattle," J Animal Sci. vol. 25, pp. 114–115.

Moody et al., "Study of Back Fat Layers of Swine", J. of Animal Sci., vol. 18, pp. 809–813 (1959).

Hazel et al. "Ultrasonic Measurement of Fatness in Swine" J of Animal Sci., pp. 815–819.

Miles, "New Equipment for Measuring the Speed of Ultrasound and its Applications in the Estimation of Body composition of Four Livestock," T. S. pp. 93–105.

Cross, "Over View of Systems Analysis for Objective Assessment of Carcass Value".

Goss et al. "Comprehensive Compilation of Empirical Ultrasonic Properties of Mammalian Tissues", J. of Acoust. Soc., Am. vol. 64, No. 2 pp. 423–457 (1978).

Gosset et al. "Compilation of Imperical Ultrasonic

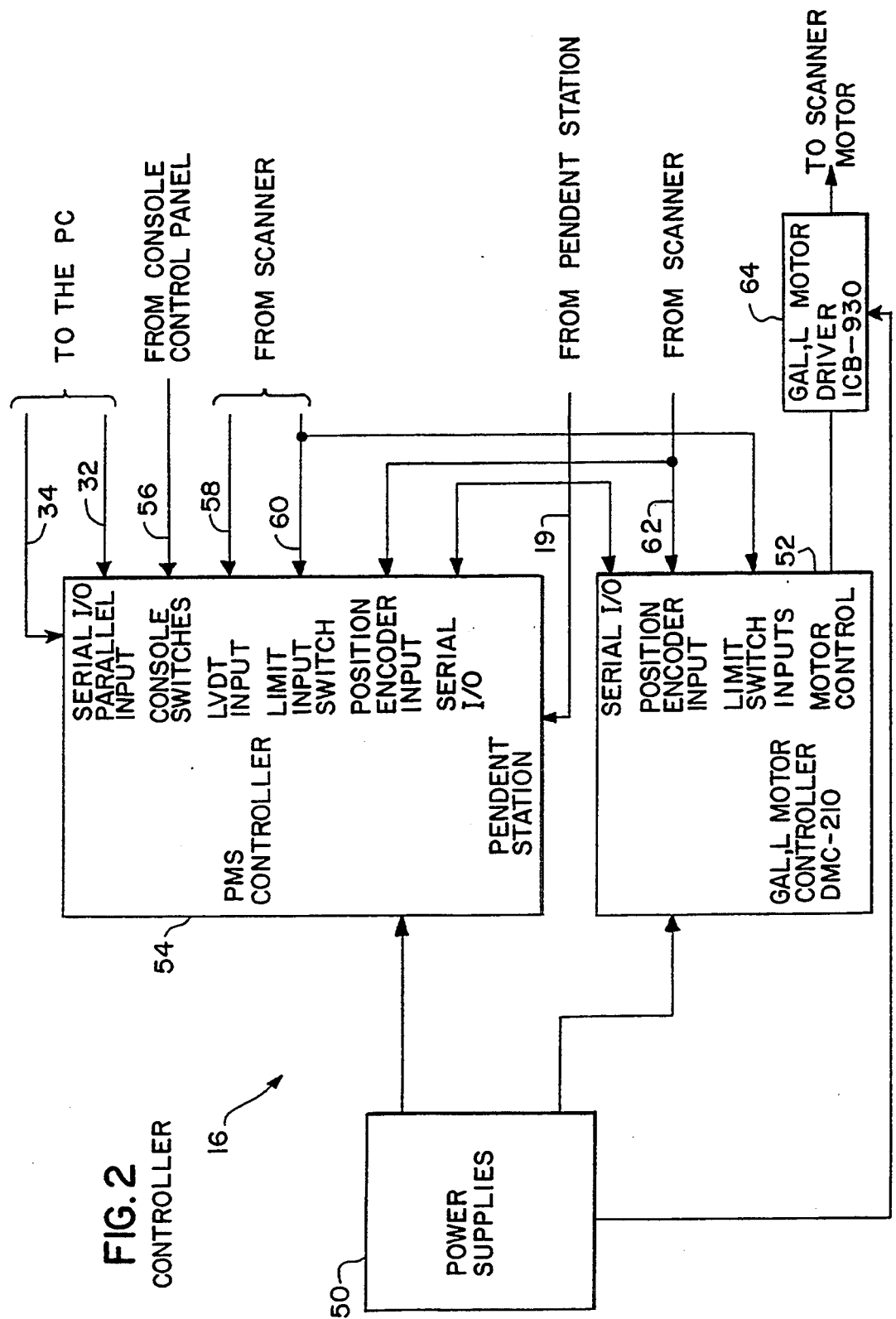
FIG. 2 CONTROLLER

X,Y COORDINATE CALCULATION $$X = \left(R - \frac{TOF_{FAT} \times V_{FAT}}{2} + \frac{TOF_{MUSCLE} \times V_{MUSCLE}}{2}\right) \times \sin\theta$$

$$Y = R - \left(R - \frac{TOF_{FAT} \times V_{FAT}}{2} + \frac{TOF_{MUSCLE} \times V_{MUSCLE}}{2}\right) \times \cos\theta$$

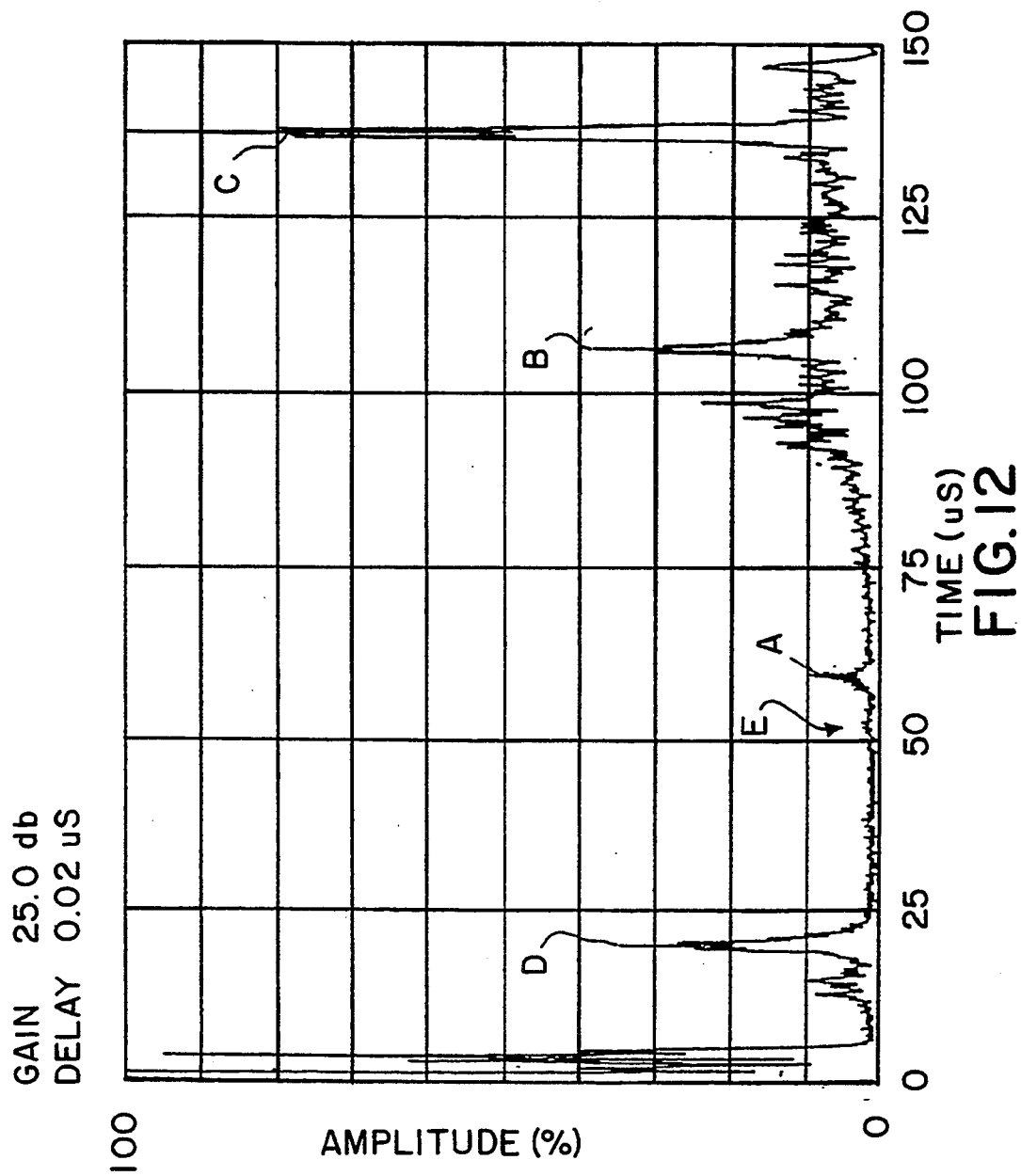

NON-INVASIVE DEVICE AND METHOD FOR GRADING MEAT

FIELD OF THE INVENTION

The present invention relates to ultrasonic measuring devices, and more particularly to a non-invasive device for determining fat thickness and longissimus muscle area (ribeye, beef or loin eye, pork) of a livestock animal and/or carcass.

BACKGROUND OF THE INVENTION

In the livestock industry, a primary factor for determining the value of a slaughtered animal carcass is the lean content of the carcass. Historically, various techniques have been devised to determine a grade or quality rating of an animal carcass. Various prior art techniques and devices are known which provide some indication of such information.

After a meat animal such as a beef or hog is slaughtered, it may be graded for lean content and/or quality by a grader who evaluates each carcass. At the present time, grading is typically done by visual inspection. Since the grade assigned to a carcass determines the value per pound for the carcass, grading has a significant economic impact. It is also well known that small variations in grading can have a large impact on the price received for a carcass.

A method and apparatus for ultrasonically grading a carcass is disclosed in U.S. Pat. No. 4,785,817 to Stouffer. The Stouffer method and apparatus include multiple transducers for ultrasonically creating a video image corresponding to a cross section of the animal carcass. The transducer head of the Stouffer device includes a linear array of transducer elements in conventional manner which are held by the transducer support unit in a generally horizontal position. The image produced by the Stouffer device is typically of the ribeye (beef) or loin eye area (pork) of the carcass. It is suggested in Stouffer that the grade of the carcass may be evaluated automatically by means of a computer using a suitable pattern recognition device which transfers information to the computer derived from the video or electronic image of the loin eye area.

Other ultrasonic devices for grading live animals and animal carcasses are disclosed in European Patent No. 0337661 to Wilson and the Carlson patents, U.S. Pat. Nos. 4,359,055 and 4,359,056. The Wilson patent discloses a hand held ultrasonic transducer unit which includes mutiple ultrasonic transducers. Scanning is preferably carried out on live animals with the Wilson device. The Wilson and the Carlson devices enable determination of skin/fat layer thicknesses and the muscle layer adjacent to the fat. The primary intent of the Carlson devices is for determining the thickness of the back fat of a live animal, particularly a pig or swine. The transducer of the Carlson device produces pulses which are amplified and supplied to a threshold detector and counted by an electric counter. The gain of the amplifier is varied in accordance with the number of counts detected by the counter device until the first fat layer is detected.

None of the aforementioned prior art devices enable precise determination of the area of the longissimus muscle of the animal as well as fat thickness in rapid fashion, i.e. in a manner rapid enough to evaluate carcasses at a rate suitable for use in a typical slaughterhouse application. Thus, an accurate high-speed, high volume device which enables a determination of carcass value relating to the grade, quality and lean content of the carcass is needed.

SUMMARY OF THE INVENTION

A non-invasive device for obtaining measurements of an animal carcass according to one aspect of the present invention comprises an ultrasonic pulser/receiver means for transmitting ultrasonic pulse signals and receiving reflected ultrasonic signals. Said pulser/receiver means producing a plurality of ultrasound signals corresponding to said received reflected ultrasonic signals. Drive means for positioning said ultrasonic pulser/receiver means along a predetermined path and in contact with the live animal or carcass. Said drive means producing a position signal corresponding to the relative position of said ultrasonic pulser/receiver with respect to the live animal or carcass, and means for analyzing said ultrasound signals and said position signal to produce a measurement corresponding to lean content of the live animal or carcass.

A non-invasive method for obtaining measurements of a live animal or carcass according to another aspect of the present invention comprises the steps of providing an ultrasound unit which contacts the live animal or carcass at predetermined locations and which emits and receives ultrasonic signals. A reflection signal is produced corresponding to received ultrasonic signals. Positioning said ultrasound unit in contact with the live animal or carcass at predetermined locations of the live animal or carcass, moving said ultrasound unit along a predetermined path while maintaining contact between said ultrasound unit and the live animal or carcass, storing said reflection signal at a plurality of locations along said predetermined path to produce a collection of stored reflection signals, and analyzing said collection of stored reflection signals are used to determine therefrom a lean content rating for the live animal or carcass.

One object of the present invention is to provide an improved method and apparatus for obtaining measurements of live animals and/or carcasses.

Another object of the present invention is to provide a more reliable and highly accurate device and method for determining animal carcass fat and lean content.

Another object of the present invention is to provide a device and method for automatically scanning a live animal or carcass and measuring longissimus muscle cross-sectional area and fat thickness as well as automatically determining lean content or lean weight from such measurements.

Yet another object of the present invention is to provide a fully automated live animal or carcass analyzing system for determining live or carcass value based upon fat/lean content of the live animal or carcass.

These and other objects of the present invention will become more apparent from the following description of the preferred embodiment.

BRIEF DESCRIPTION OF THE DRAWINGS

FIG. 2 is a block diagram depicting the components of the controller 16 of FIG. 1.

FIG. 3b is a rear view of the fixture shown in FIG. 3a.

FIG. 12 is a chart depicting the electronic "full-video" signal produced by the instrument 12 at a location 1 inch from the midline of pork (live or carcass).

DESCRIPTION OF THE PREFERRED EMBODIMENT

Figure 1:
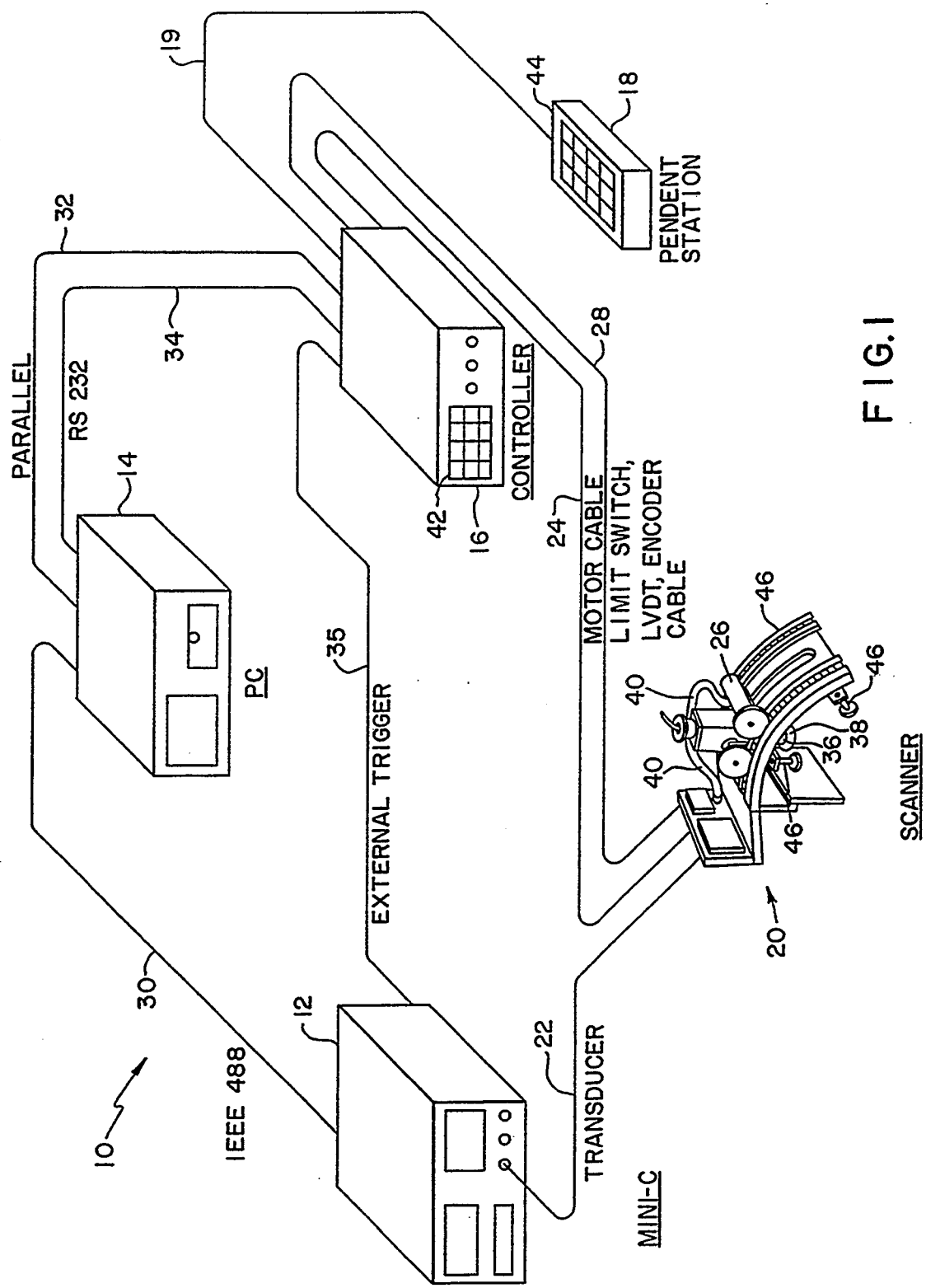
FIG. 1 is a diagrammatic illustration of a non-invasive meat grading device according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3A:
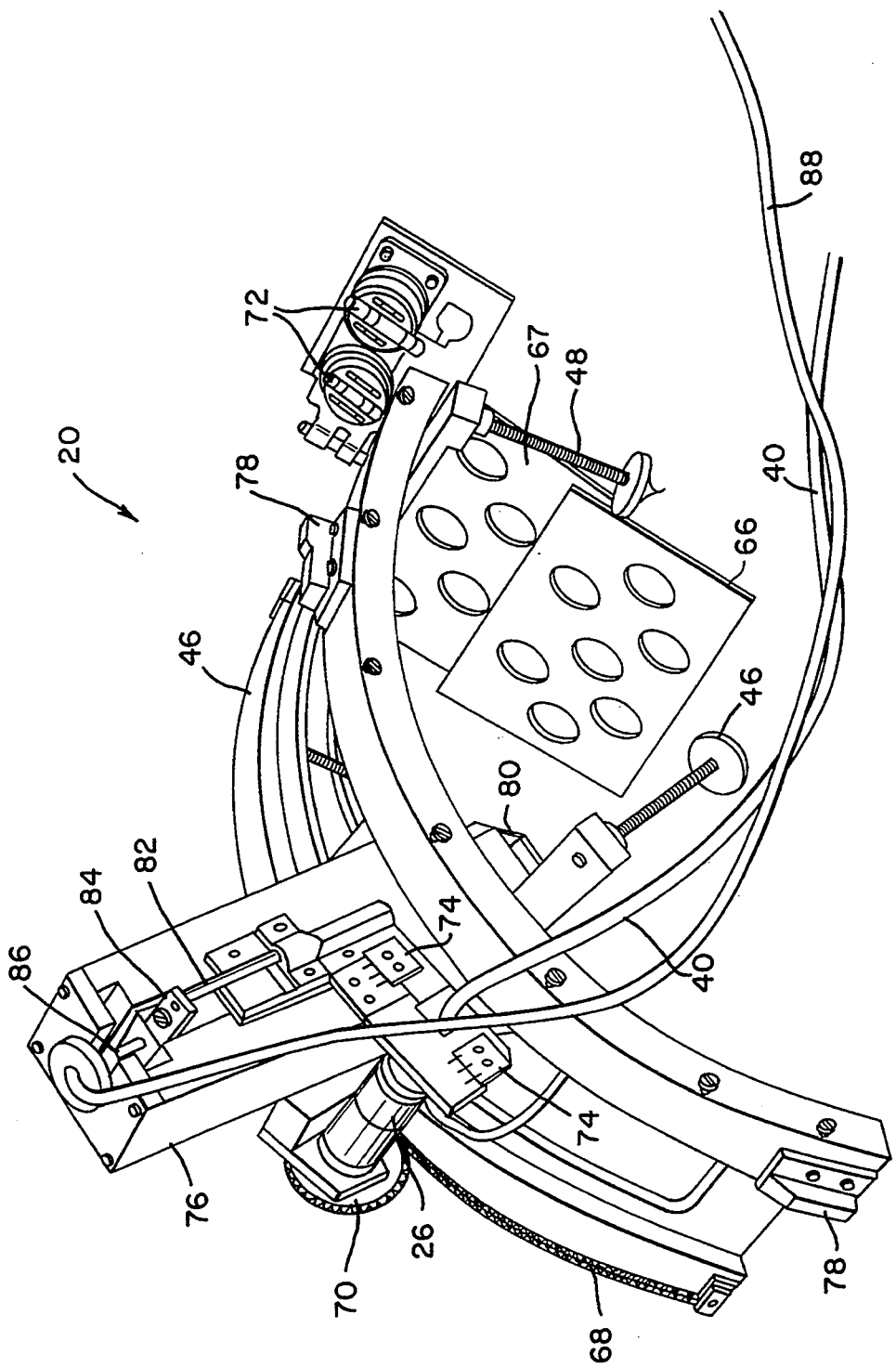
FIG. 3a is a front view of a fixture according to the present invention.

Referring now to FIG. 1, a diagrammatic illustration of a non-invasive meat grading device 10 according to the present invention is shown. The meat grading device 10 includes an ultrasonic data acquisition instrument 12, a personal computer 14, a controller 16, a remote control operator keyboard or pendent station 18 and a fixture 20. An ultrasonic transducer (shown in FIG. 3a) is connected to instrument 12 via signal path or multi-conductor cable 22. Motor 26 receives control signals from controller 16 via multi-conductor signal path 24. Similarly, limit switch signals, LVDT (linear voltage differential transformer) signals and encoder signals are carried by signal path 28 which is also a multi-conductor cable. The limit switches, LVDT device, and encoder are shown in FIGS. 3a and/or 3b. An IEEE 488 or GPIB interface 30 provides a data interface between instrument 12 and computer 14. A parallel interface bus 32 interconnects controller 16 and computer 14. A serial interface 34 between computer 14 and controller 16 is shown and is typically an RS 232 serial interface. A trigger signal is supplied from controller 16 to instrument 12 via signal path 35.

Operationally speaking fixture 20 is located in such a manner that a live animal (not shown) or carcass (not shown) can be placed in close proximity to the ultrasonic transducer 36. A rubber boot 38, attached over the transducer 36, provides a fluid chamber into which water or other suitable couplant is supplied to provide proper or adequate ultrasonic coupling between the transducer 36 and the live animal or carcass. Couplant is supplied to the chamber created by the rubber boot 38 via a hose 40. Pressurized couplant is supplied to a hose 40 from a pressurized source (not shown). Switches or keypad 42 of controller 16 and switches or keypad 44 of remote control 18 provide operator interface capability for controlling the device 10 in manual mode operation, automatic mode operation, diagnostics mode operation, and calibration mode. Switches 42 and 44 provide identical functional capability.

Basic operation of the entire system or device 10 is orchestrated or synchronized by controller 16. Controller 16 receives setup commands from the operator for automatic operation or scanning of the live animal or carcass, typically a beef or pig. Next, the operator initiates scanning of the live animal or carcass. The controller 16 moves the transducer 36 (via motor 26) to a series of predetermined locations and triggers instrument 12 to acquire an ultrasonic A scan. As each A scan is acquired, the instrument 12 processes the A scan signal by digitizing the signal into approximately 8000 bytes of data and altering the data according to predefined software modes of operation present in instrument 12. When the digitized A scan is processed, the instrument 12 indicates to computer 14 that data is ready, and computer 14 reads the data in over the interface 30. Thus, a most effective use of cycle time is made by analyzing the data as soon as it is available for each scan. If the computer 14 is unable to accept additional data from the instrument 12, a signal is supplied to the controller 16 to prevent further triggering of the instrument 12 until the most recent A scan data is processed by computer 14.

Automatic mode of operation enables execution of predetermined scan plans. The first step in setting up operation in automatic mode is to write, download and debug a scan plan. At the present time, a scan plan is defined as follows: for the first two inches an ultrasonic scan will be performed and digitized every ⅛ inch; for the next two inches a scan will be taken every quarter inch; and for the final two inches, or until the end of the movement of the transducer, a scan will be performed and digitized every ⅛ inch. Optionally, a menu selection system enables the operator to select one of several scan plans previously recorded in memory of the controller 16 to execute so that changeover from pork to beef will be as easy as selecting a new menu item. A manual mode of operation permits the operator to move the ultrasonic scanner device anywhere in the scan region and obtain information from the digitized ultrasonic scan. The transducer can be moved in the forward and reverse directions by pressing and holding buttons or switches in the keypad 42 or keypad 44. When the transducer is at the desired location, the operator can take data by pressing another button. Transducer 36 has resolution of movement down to the finest increment that the hardware permits, which is about 0.01 inches.

In calibration mode the transducer is placed in the fixture and is excited with a known signal. The signal returned will have a peak at a known position. The gain of the instrument 12 is then automatically adjusted to put the peak at the desired level. Other calibration set-ups may require determining time offsets in terms of delay as well as the window of time analysis for the ultrasonic A scan signal. In addition, diagnostics routines will be executed upon power up or upon request from the operator if desired.

In automatic mode of operation, certain setup steps must be executed by the operator before commencing automatic operation. For instance, the live animal or carcass number might be entered through the switches 40 or keyboard 44. The mode of operation of the scanner would also be selected through a menu driven program executing on the computer 14. Finally, the operator may initially desire to move the transducer 36 to a particular starting position using a jog mode activated via the keypad 44. Finally, the operator would press a start button on the keypad 42 or keypad 44 to initiate the scanning.

Once a live animal or carcass has been positioned in close proximity to transducer 36 and against legs 48, the operator activates one of the switches of keypads 42 or 44 to commence ultrasonic scanning. At that point, controller 16 triggers instrument 12 via signal path 34 to emit a pulse of ultrasonic energy into the live animal or carcass and analyze or message the reflected ultrasonic signals picked up by transducer 36. Instrument 12 digitizes the reflected ultrasonic signal and analyzes the signal in accordance with previously programmed set up modes. Computer 14 is programmed to interrogate instrument 12 and receive data via GPIB/IEEE 488 bus 30. Computer 14 is continually polling instrument 12 during scanning in order to determine whether data is available concerning a recent ultrasonic A scan. When data is supplied by instrument 12 to computer 14, computer 14 analyzes the data which is a digitized representation of the ultrasonic signal reflection from the live animal or carcass and the muscle/fat interface layers are detected by analyzing the digitized reflected signal.

Controller 16 then moves the transducer along the arc of the fixture and triggers instrument 12 again to produce another A scan set of information or data. Again the data is supplied via interface 30 to computer 14 for analysis. In this fashion, motor 26 moves the transducer 36 in accordance with signals from controller 16 along the curved member 46 of fixture 20 until a sufficient number of scans has been gathered and, generally speaking, the transducer has moved entirely across the live animal or carcass. When computer 14 is unable to immediately input data from instrument 12, controller 16 is informed of the delay via the parallel interface 32 or the serial interface 34 and movement of the transducer is momentarily halted until the delay is resolved (calculations are completed). Computer 14 then determines the area of the longissimus muscle or thickness of the fat layers. Longissimus muscle, fat thickness and longissimus muscle depth may individually or in combined fashion be used in a prediction equation to produce a grade or lean content rating of the live animal or carcass. The lean content rating is used to determine live animal or carcass value. Additionally, an ultrasound scan of the ham area of a pork animal or carcass and round area of a beef carcass provides additional information for use in a prediction equation to determine animal or carcass lean content and/or value.

Prediction equations (such as the following) have been developed by Purdue University research staff and are well known in the livestock industry for predicting "percentage lean content" and "weight of lean" of a pork carcass. These equations are from Orcutt et al. *Journal of Animal Science*, Vol. 68, Page 3987, 1990, which article is hereby incorporated by reference.

$$\text{Kg of lean} = 2.67 + .45 \text{ Hot Carcass Weight (kg)}$$
$$- 3.31 \times \text{10th rib Fat Depth, 3/4 (cm)}$$
$$+ .29 \times \text{10th rib Loin Muscle Area (cm}^2\text{)}$$

$$R^2 = .83$$
$$RSD = 1.99$$

Similar equations are also known for beef and have been adopted by the USDA and incorporated into agency standards. The USDA equations for beef are:

$$\% \text{ cutability} = 51.34 - (5.78 \times \text{12th rib fat thickness, in.})$$
$$- (0.0093 \times \text{Hot Carcass Weight, lbs.})$$
$$- (0.462 \times \% \text{ Kidney, pelvic and Heart fat})$$
$$+ (0.740 \times \text{Ribeye area, in}^2)$$

$$\text{Yield Grade} = 2.5 + (0.25 \times \text{12th rib fat thickness, in.})$$
$$+ (0.0038 \times \text{Hot Carcass Weight, lbs.})$$
$$+ (0.2 \times \% \text{ Kidney, pelvic and Heart fat})$$
$$- (0.32 \times \text{Ribeye area, in}^2)$$

The radius of curve member 46 is approximately 8.2 inches. This radius permits the transducer to travel in an arch which corresponds closely with the radius of a live animal or carcass as measured from the midline or backbone of the live animal or carcass. Further details regarding the location at which ultrasonic scans are executed is presented in conjunction with the discussion of FIG. 4.

The ultrasonic data acquisition instrument 12 is a model 1740/1750 Mini-C device available from Systems Research Laboratories, Inc. a division of Arvin/Calspan, 2800 Indian Ripple Road, Dayton, Ohio 45440. The Mini-C device is capable of "massaging" A scan data and rectifying an A scan signal digitally to provide maximum amplitude deviations indicative of tissue interfaces. Such massaging occurs when the instrument 12 is programmed to produce "radio frequency" mode data (see FIGS. 12–16). Alternately, instrument 12 produces "RF" scan signals (see FIGS. 12A–16A) which are digitized for analysis. Computer 14 is a personal computer which includes hard disk and floppy disk capability, ROM, RAM, serial and parallel I/O, IEEE 488 GPIB interface board, at least one Meg of RAM, and an Intel 80286 microprocessor based motherboard including a math coprocessor. Computer 14 also includes a monitor, printer, and disk controller board. The transducer shown is a model No. 1LD-0106-GP available from Technisonic. Ultrasonic transducers typically operate in the range of 0.5–7.5 megaHertz. This system is designed to operate with a variety of transducers with frequencies ranging from 0.5 to 7.5 megaHertz.

Figure 3B:
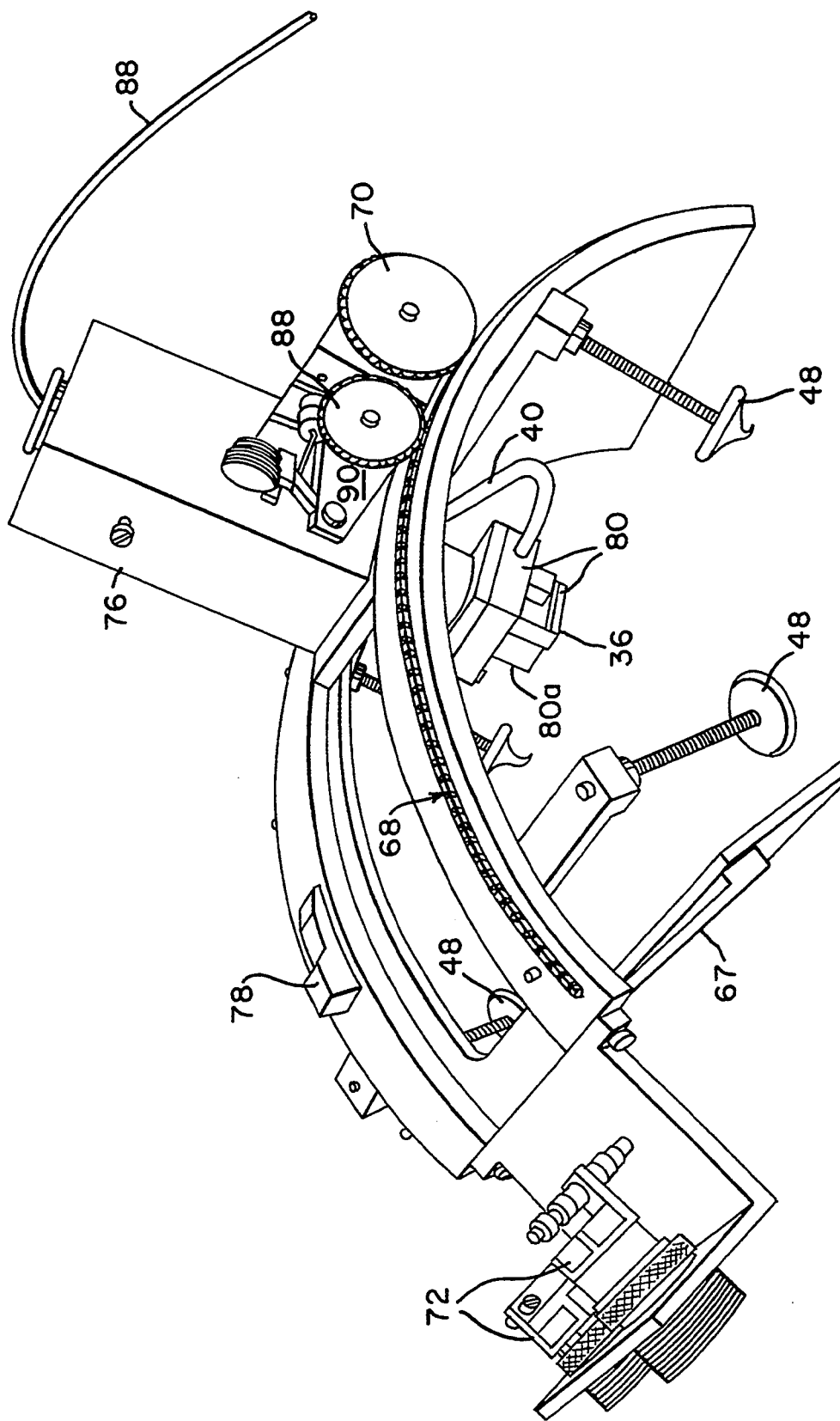

Referring now to FIG. 2, a more detailed block diagram depicting the components of controller 16 is shown. Controller 16 includes power supplies 50, a motor controller board 52 manufactured by Galil (model no. DMC-210) and a controller board 54 which includes a microcomputer having serial I/O capability, an A/D converter, parallel I/O, ROM, and RAM. Signals and data exchanged between computer 14 of FIG. 1 and controller 16 take place over signal paths 34 and 32. For example, the voltage from a LVDT (not shown in FIG. 2) is digitized by controller board 54 and supplied to computer 14 via serial interface 34. Switches 42 are monitored by controller board 54 via switch matrix scanning I/O lines in signal path 56. A LVDT, linear voltage differential transformer, is connected to controller board 54 via signal path 58. The LVDT, shown in FIG. 3a, provides linear displacement information or signals to controller 16, which information is forwarded to computer 14 for use in determining transducer position and calculating longissimus muscle area. Thus, when the live animal or carcass does not correspond with the radius of curved member 46, the LVDT device provides radial position information used to locate tissue interface boundaries and accurately calculate fat thickness and longissimus muscle area. In addition, limit switch signals are supplied from the fixture 20 to controller board 54 via signal path 60 and to the motor controller board 52. Limit switches 74, shown in FIG. 3a, prevent over-travel of the transducer with respect to the fixture and are well known in the art for preventing damage to a motor driven device. Signals from the rotary encoder 90, shown in FIG. 3b, provide displacement information to the controller board 54 and the motor controller 52 via signal path 62. The signals present on signal path 62, signal path 60, and signal path 58 are all represented by signal path 28 in FIG. 1. Pendent station 44 is connected to controller board 54 via signal path 19 as shown in FIG. 1. Also shown in FIG. 2 is a motor driver board 64 from Galil model no. ICB-930. The motor driver board 64 receives power from power supplies 50 and signals from motor controller 52. Motor driver board 64 supplies drive signals to motor 26 to position the transducer properly in relation to the animal carcass along the curved member 46. Power supplies 50 also supply power to driver board 64 and the controller board 54.

Figure 11:
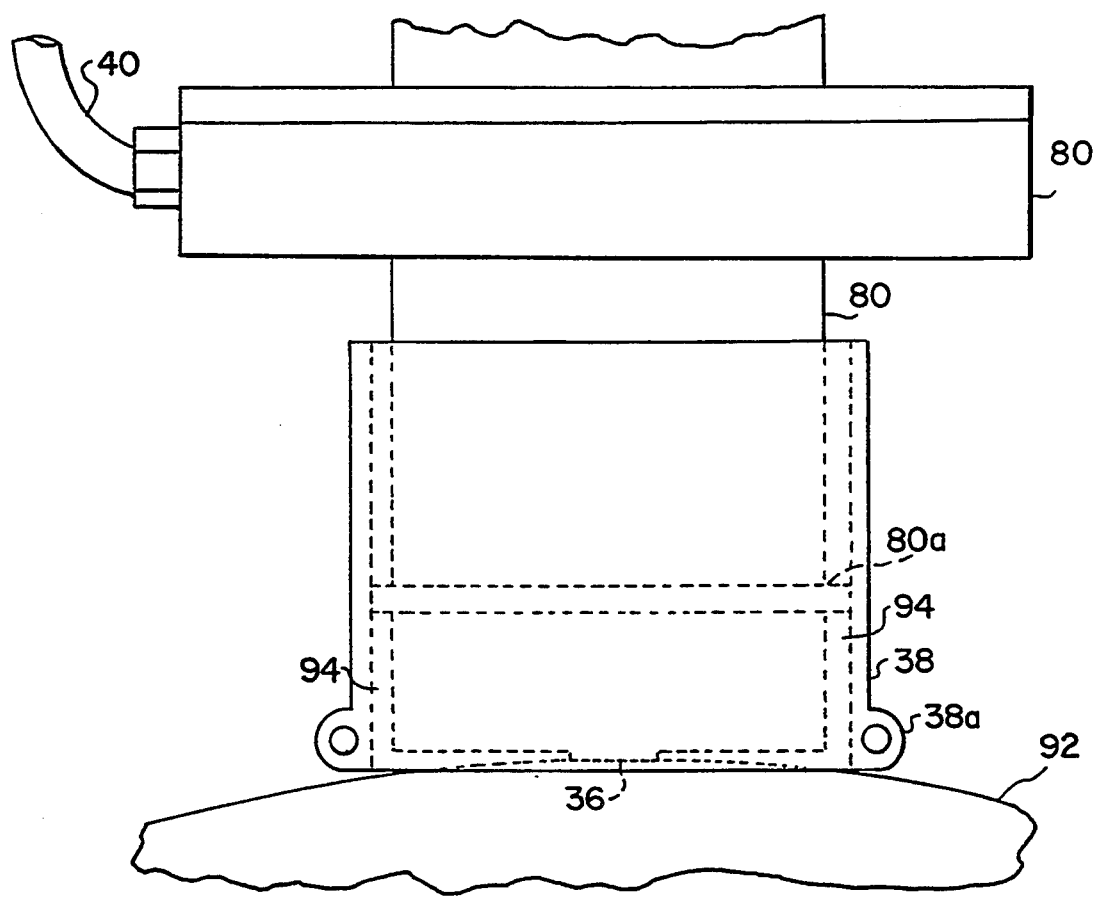
FIG. 11 is a partial enlarged view of the ultrasonic sensor and rubber boot shown in contact with a live animal or carcass.
Figure 12A:
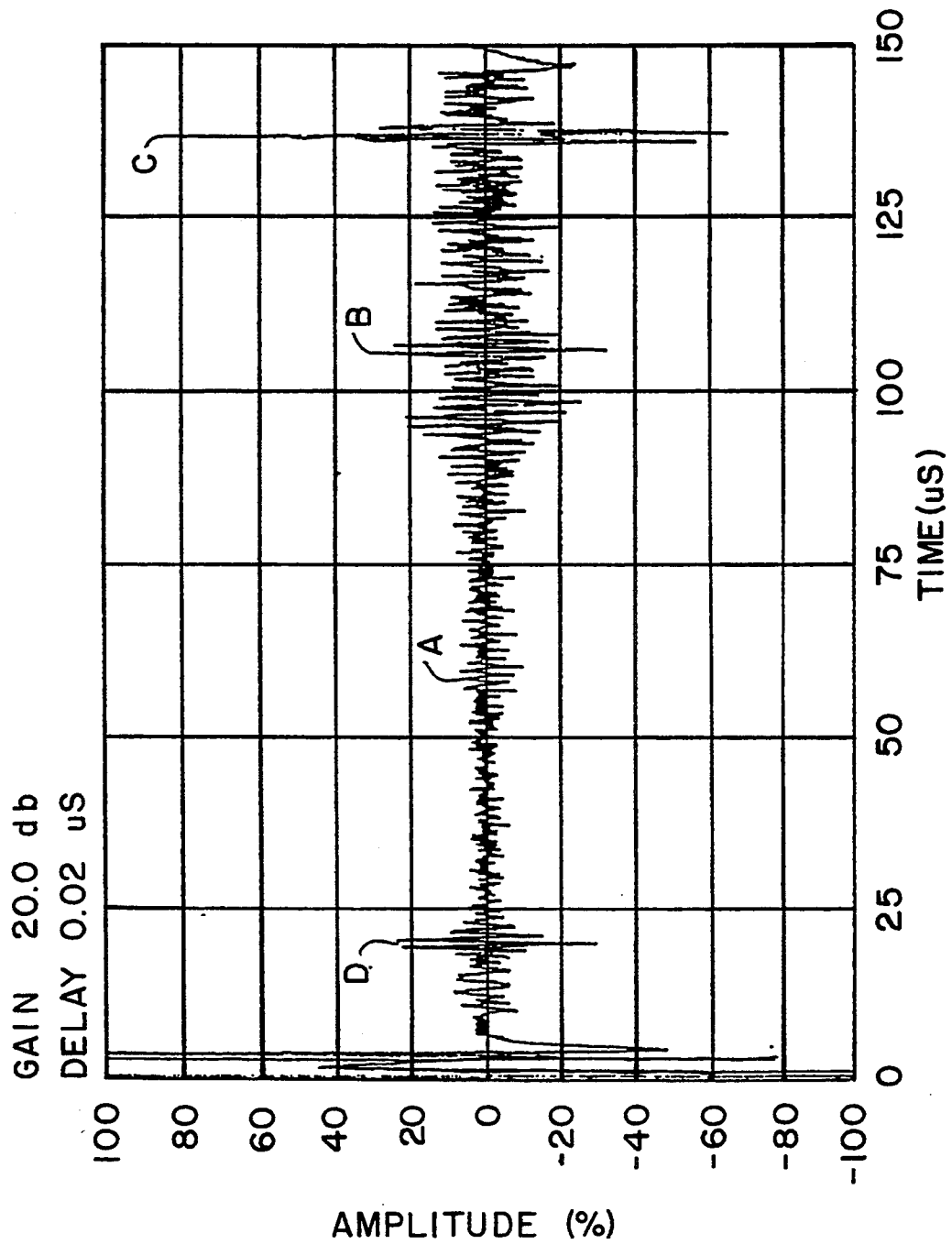
FIG. 12A is a chart depicting the electronic "RF" signal corresponding to FIG. 12 produced by the instrument 12 at a location 1 inch from the midline of pork (live or carcass).
Figure 13:
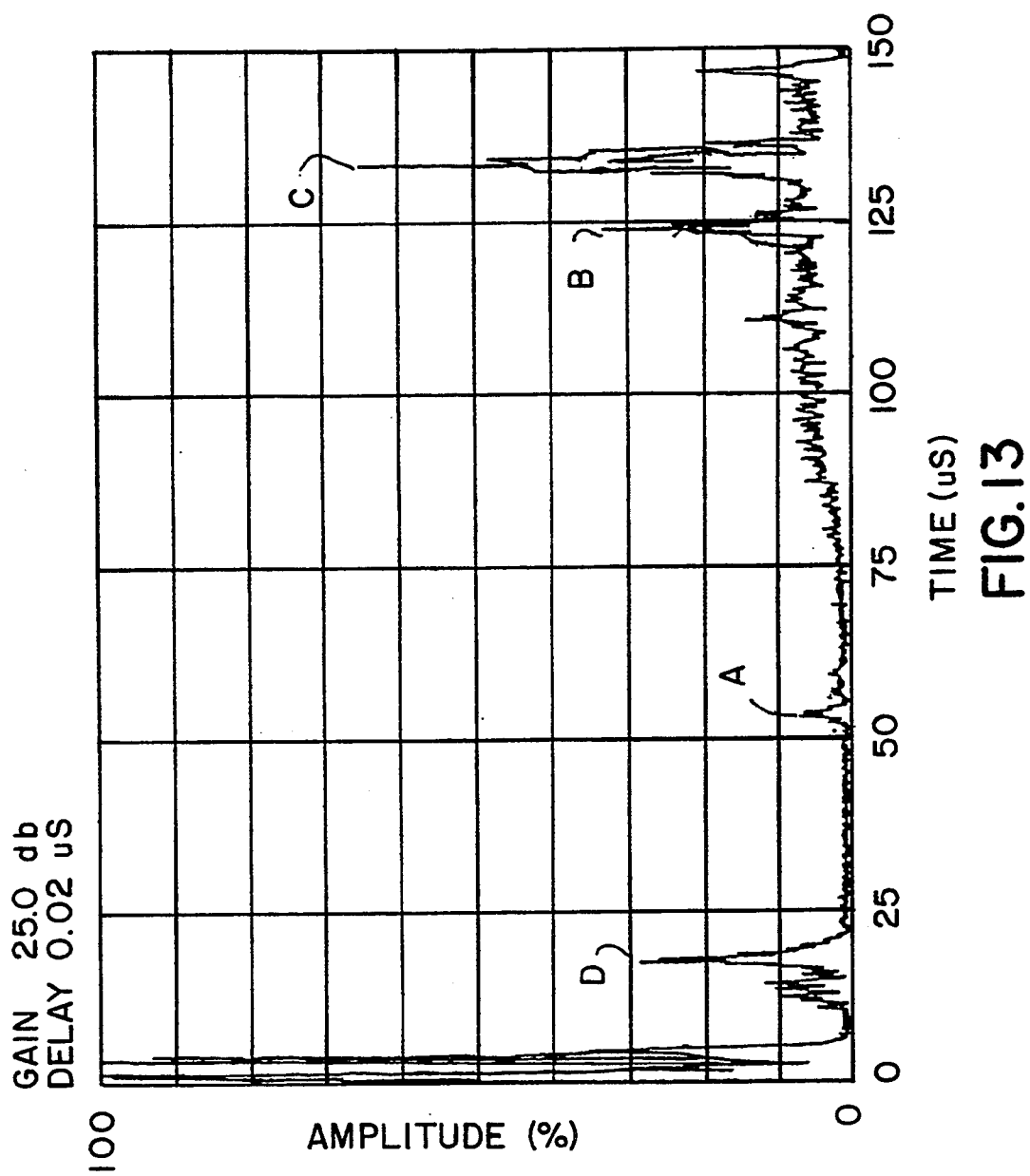
FIG. 13 is a chart depicting the electronic "full video" signal produced by the instrument 12 at a location 2 inches from the midline of pork (live or carcass).
Figure 13A:
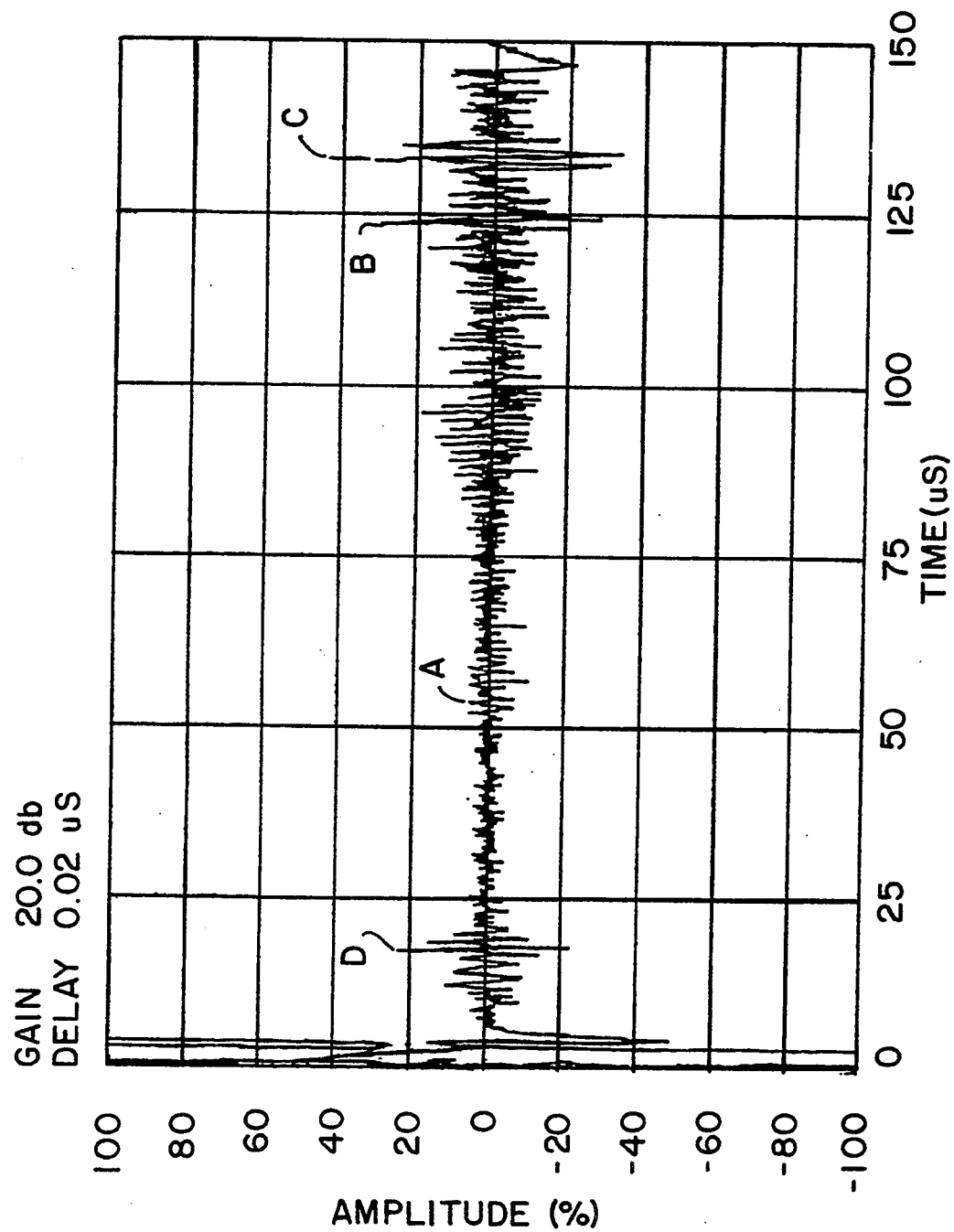
FIG. 13A is a chart depicting the electronic "RF" signal corresponding to FIG. 13 produced by the instrument 12 at a location 2 inches from the midline of pork (live or carcass).
Figure 14:
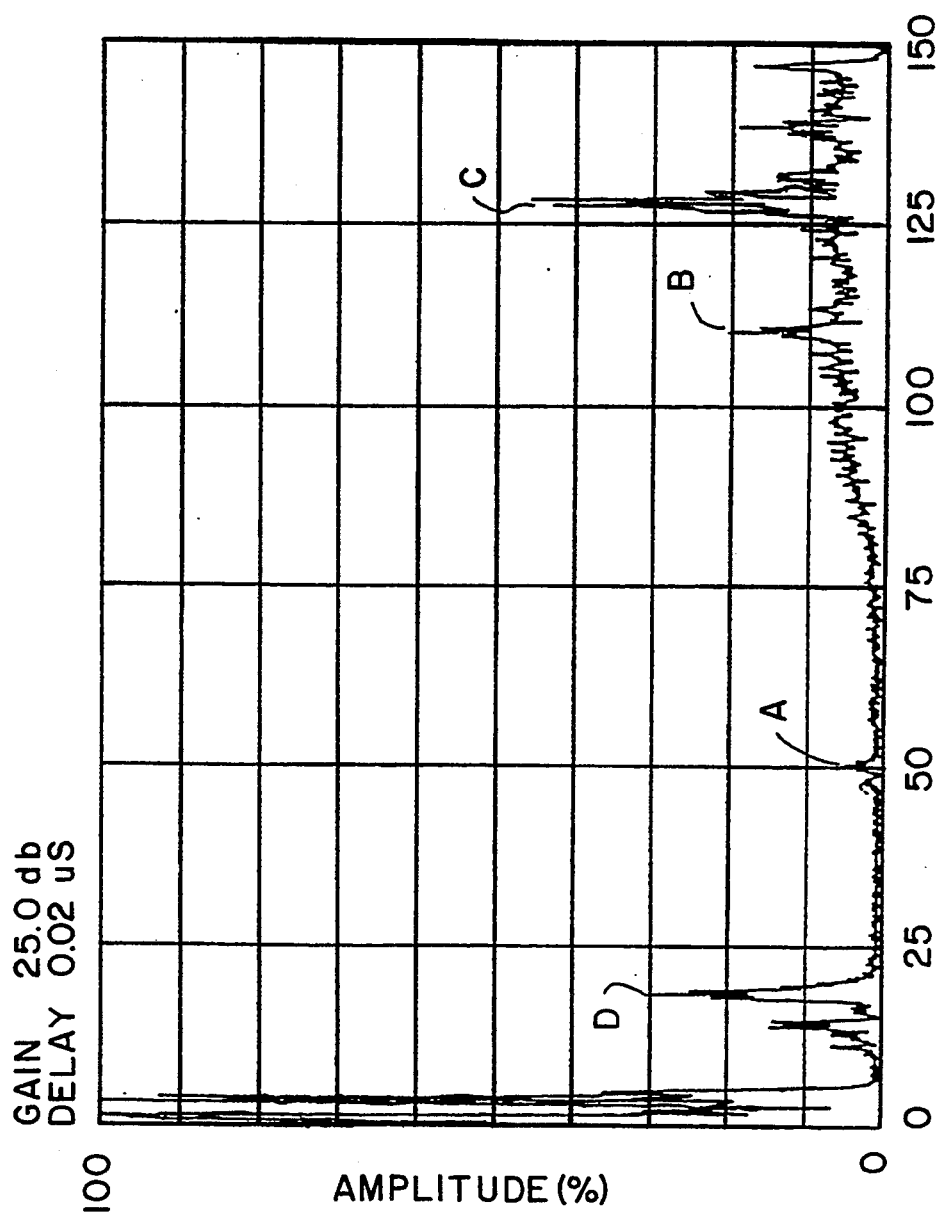
FIG. 14 is a chart depicting the electronic "full video" signal produced by the instrument 12 at a location 3 inches from the midline of pork (live or carcass).
Figure 14A:
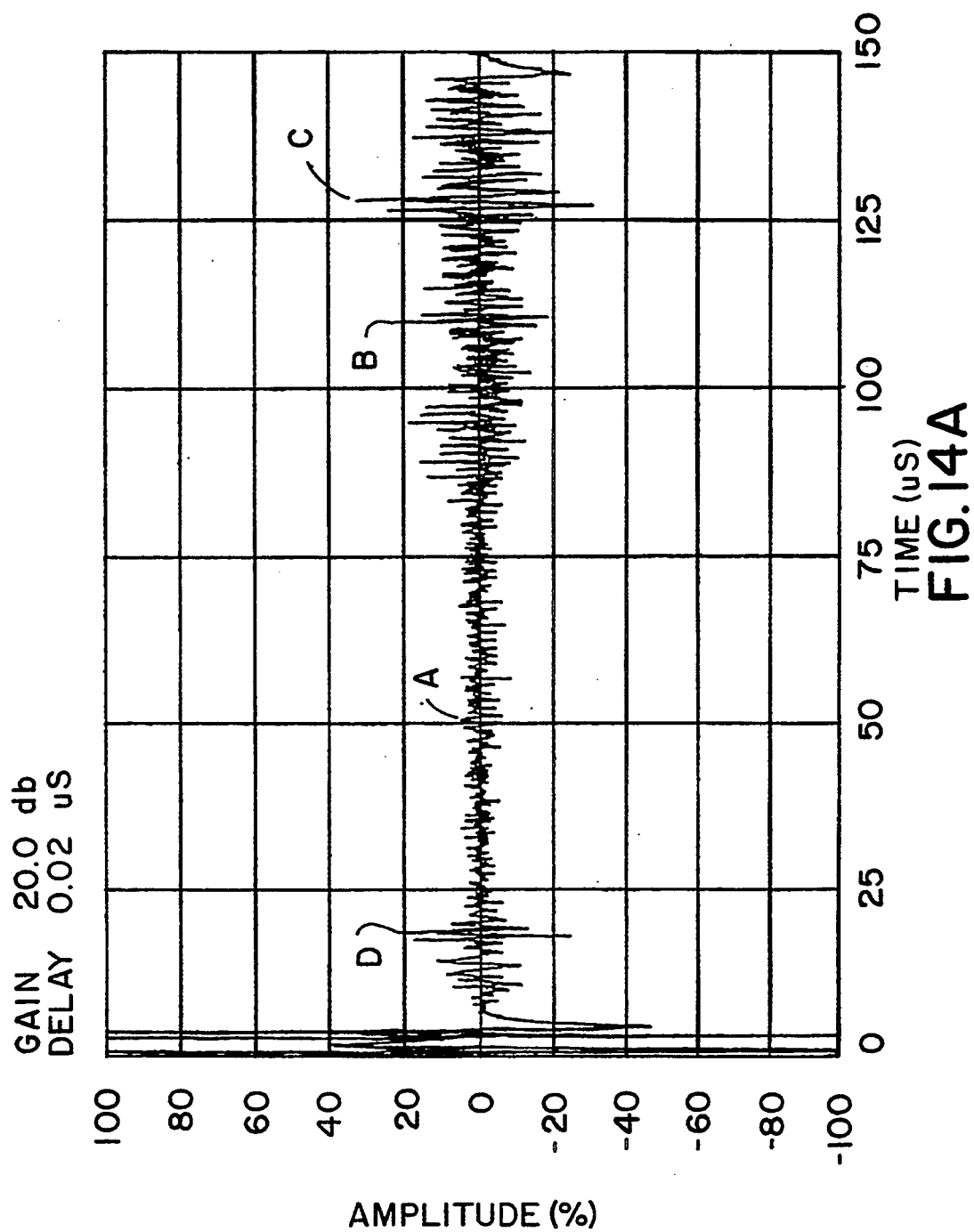
FIG. 14A is a chart depicting the electronic "RF" signal corresponding to FIG. 14 produced by the instrument 12 at a location 3 inches from the midline of pork (live or carcass).
Figure 15:
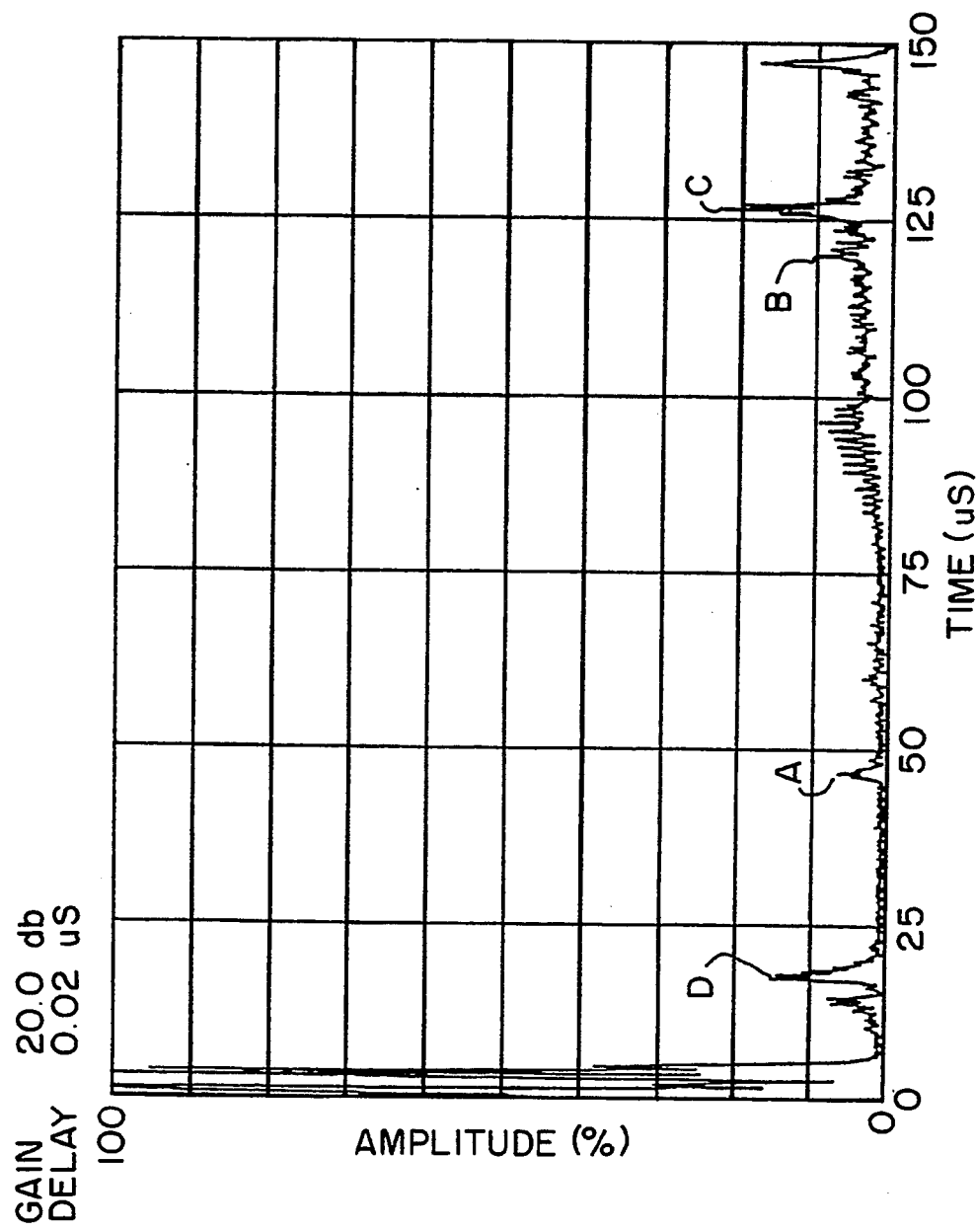
FIG. 15 is a chart depicting the electronic "full video" signal produced by the instrument 12 at a location 4 inches from the midline of pork (live or carcass).
Figure 15A:
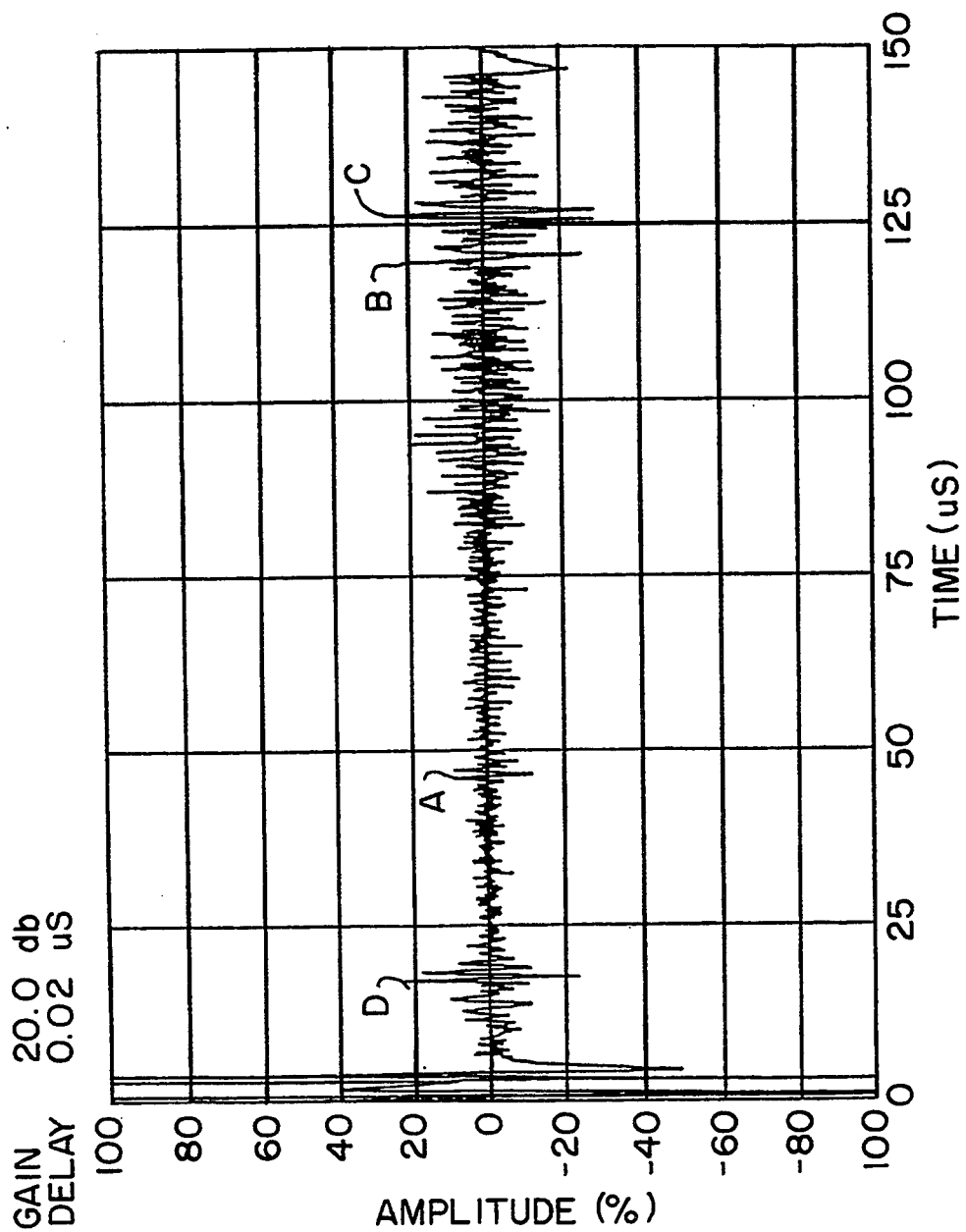
FIG. 15A is a chart depicting the electronic "RF" signal corresponding to FIG. 15 produced by the instrument 12 at a location 3 inches from the midline of pork (live or carcass).

Referring now to FIGS. 3a and 3b, the fixture 20 according to the present invention is shown. Plate 66 is attached to plate 67. Plate 67 is attached to curved member 46. Plates 66 and 67 provide a physical locating point for positioning the live animal or carcass with respect to the fixture 20. Essentially, the live animal or carcass of a pig or beef is positioned so that the split line or midline rests against plates 66 and 67. In so doing, the live animal or carcass midline or backbone is positioned so that the radial center of curved member 46 corresponds approximately with the location of the midline or backbone of the live animal or carcass. On the top surface of curved member 46, a chain 68 provides a positive mechanical traction interface between the top surface of curved member 46 and drive motor 26. A sprocket 70 enables positive mechanical action between the shaft of motor 26 and the chain 68. Legs 48 provide positive locating reference points for the live animal or carcass to rest against when positioned adjacent fixture 20. Connectors 72 provide convenient electrical connection devices for establishing electrical connections between instrument 12 and fixture 20 as well as between controller 16 and the electrical/electronic devices mounted on fixture 20. Electrical connections to fixture 20 correspond with the signal paths and signals carried thereon designated 22, 24 and 28 in FIG. 1. Limit switches 74 are positioned to prevent overtravel of the transducer mounting 76 with respect to curved member 46. Limit switches 74 are activated by cams 78 near the end of travel limits of the transducer mounting 76. The transducer mounting 76 is moved along the curved member 46 by drive motor 26. Mechanical attachment means well known in the art enable freedom of movement between the transducer mounting 76 and the curved member 46 so that the transducer mounting 76 may move along the outer arc of curved member 46 in response to rotation of motor 26. Water manifold 80, shown in more detail in FIG. 11, is attached to and moves radially with the ultrasonic transducer. The manifold 80 surrounds the tip of the ultrasonic transducer. Water manifold 80 provides a conduit for water or other suitable couplant to the area between the transducer and the live animal or carcass to enable ultrasonic signal coupling between the transducer and the live animal or carcass. Rubber boot 38 is not shown in FIGS. 3a and 3b, however it is shown in greater detail in FIG. 11.

The mechanical actuator of LVDT 82 is mechanically connected to arm 84. Arm 84 is connected to transducer 36 and moves radially with respect to curved member 46 in conjunction with variations in the radial surface of the live animal or carcass. Thus, by way of LVDT 82, a signal is available indicative of the transducers radial location ("R" of FIG. 4) with respect to the live animal or carcass, thereby aiding in "normalizing" the radial location of the transducer with respect to reference coordinate locations to enable calculating fat thickness and longissimus area with a high degree of accuracy. Spring 86 urges the transducer, mounted within transducer mounting 76 so that the transducer moves freely in a radial direction, toward the animal or carcass so that the rubber boot 38 is pressing against the live animal or carcass with a light force such as two to three grams. The contact force of the boot against the live animal or carcass helps maintain a reservoir of water or suitable couplant in the area between the transducer and the live animal or carcass to aid in signal coupling between the transducer and the live animal or carcass. Hose 40 supplies pressurized water or suitable couplant to the couplant manifold 80. Cable 88 contains the conductors which provide an electrical connection between the transducer 36 and the ultrasonic data acquisition instrument 12. Sprocket 88 is mounted on the shaft of encoder 90. Encoder 90 provides feedback information to the motor controller 52 of FIG. 2 and to the controller board 54. Couplant manifold 80 includes a lip 80a to facilitate a good seal between the boot, shown in FIG. 11, and the couplant manifold 80.

The miniature incremental rotary optical encoder 90 is a model E116 available from BEI Motion Systems Company, Computer Products Division, San Marcos, Calif. 92069. The drive motor 26 is a model A-1430 permanent magnet planetary gear motor available from TRW. The LVDT is a MHR series miniature device model number SMS/GPM-109A available from Schaevitz, 7905 N. Rte. 130, Pennsavken, N.J. 08110.

The motor controller 52 of FIG. 2 enables convenient programming of the motor 26 to move the transducer mounting 76 to a desired scanning position. Various motion control systems well known in the art may be substituted therefor.

Figure 4:
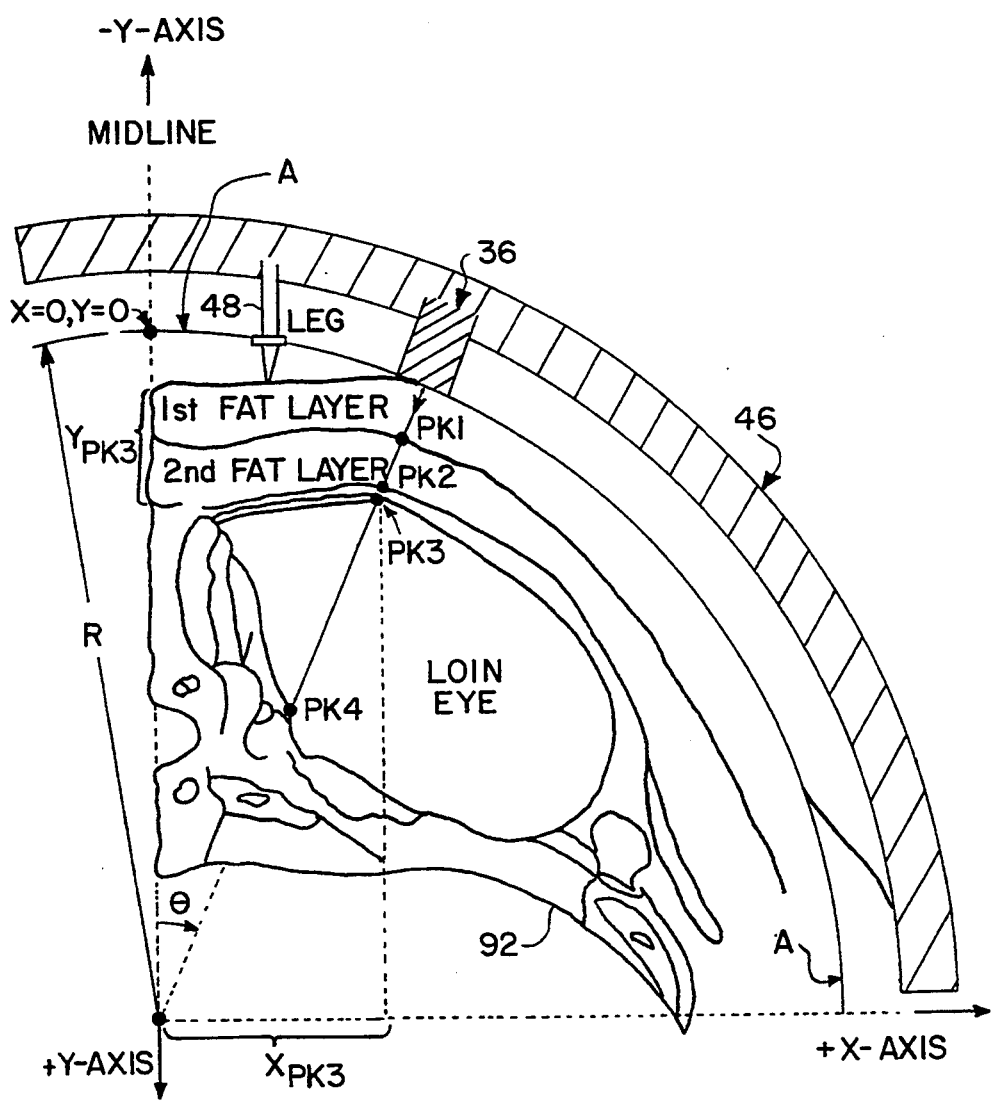
FIG. 4 is an illustrative cross-sectional view of the rib/loin area of a live animal or carcass located adjacent the fixture of FIGS. 3a and 3b.

Referring now to FIG. 4, a cross section of the curved member 46 is shown in close proximity to a rib/loin area cross-section of a live animal or carcass 92. The mathematical relationships which are established when the live animal or carcass 92 is positioned appropriately in close proximity with curved member 46 are shown in FIG. 4. An origin reference point labeled $X=0$, $Y=0$ provides a reference point from which the calculations are based in conjunction with the radius R whose central axis is located at a point so that the live animal or carcass is appropriately oriented. Typically, the radius R is between 5 ⅜ inches and 6 ⅜ inches in length. As the transducer 36 is moved along curve A, ultrasound signals are transmitted into the live animal or carcass 92 and the reflections are detected by instrument 12. The X, Y coordinates of the locations PK1, PK2, PK3 and PK4 (corresponding to tissue interface peaks 1, 2, 3 and 4) are determined according to the formulas shown below which are also shown in FIG. 4.

$$X = \left( R - \frac{(TOF_{fat})(V_{fat})}{2} + \frac{(TOF_{muscle})(V_{muscle})}{2} \right) \text{SIN}\Theta$$

$$Y = R - \left( R - \frac{(TOF_{fat})(V_{fat})}{2} + \frac{(TOF_{muscle})(V_{muscle})}{2} \right) \text{COS}\Theta$$

TOF is an abbreviation for time-of-flight of the ultrasonic signal and V represents velocity of the ultrasonic signal in the corresponding tissues. Subscripts for fat and muscle indicate that time-of-flight and velocity are in fat or muscle for calculating the X and Y coordinates of locations PK1 through PK4. The angle $\Theta$ is the angle between the midline or Y axis and the location of the transducer 36 at any time during the scanning process.

As the various peaks (PK1-4) are located in each scan, the software executed by computer 14 determines the thickness of the first and second and third fat layers as well as the radial location of the front and rear surface of the longissimus muscle as the transducer 36 moves along the curved member 46 and scans are performed. In so doing, a number of points are obtained or determined which define the area of the longissimus muscle. More particularly, the points at which ultrasound scans are taken are, for example, every ⅛ inch along the radius for the first two inches that the transducer 36 moves away from the midline, every ¼ inch for the second two inches along the radius as the transducer moves along the curved member, and every ⅛ inch for the last two inches or until the end of travel of the transducer 36 along the curved member 46.

Figure 5:
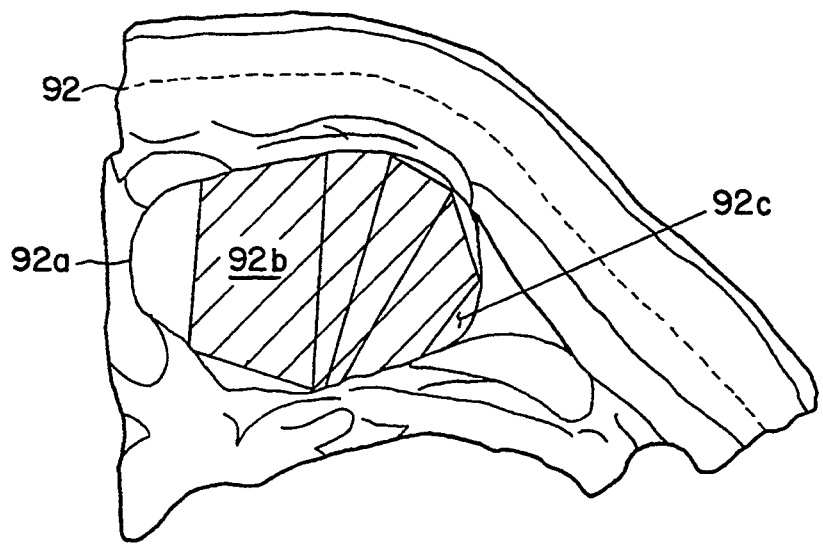
FIG. 5 is a cross-sectional view of a live animal or carcass showing the longissimus muscle area divided into three basic areas.

Referring now to FIG. 5, a rib/loin area cross section of the live animal or carcass 92 is shown wherein three areas of the longissimus muscle are labelled 92a, 92b, and 92c. These areas are hereinafter referred to as dorsal longissimus muscle area 92a, main longissimus muscle area 92b and ventral longissimus muscle area 92c. The area of the main longissimus muscle area 92b is calculated by determining the area contained within a series of adjacent quadrilaterals defined by peaks PK3 and PK4 and adding the areas together. The areas of the dorsal longissimus muscle area 92a and the ventral longissimus muscle area 92c are approximated in accordance with the following formulas. If the dorsal longissimus muscle thickness (measured along the inner edge of the dorsal longissimus muscle 92a) is greater than or equal to 1.2 inches, then the longissimus muscle area of the dorsal longissimus muscle is equal to 1.44 X (the loin eye thickness-1) square inches. If the dorsal longissimus muscle thickness is greater than 0.5 inches and less than 1.2 inches, then the area of the dorsal longissimus muscle 92a equals 0.41 X (the loin thickness-0.21) square inches. If the dorsal longissimus muscle thickness is equal to or less than 0.5 inches then the area for the dorsal longissimus muscle area 92a is 0 square inches.

The ventral longissimus muscle area 92c is calculated according to the following formulas. If the ventral longissimus muscle thickness (measured along the inner edge of the ventral longissimus muscle 92c) is greater than or equal to 1.7 inches, then the longissimus muscle area is equal to 2.2 X (the longissimus muscle thickness-3.3) square inches. If the ventral longissimus muscle thickness is greater than 0.5 inches and less than 1.7 inches then the longissimus muscle area for the ventral longissimus muscle equals 0.36 X (the longissimus muscle thickness-0.18) square inches. If the ventral longissimus muscle thickness is less than 0.5 inches, then the area for the ventral longissimus muscle is considered to be 0 square inches.

Figure 6:
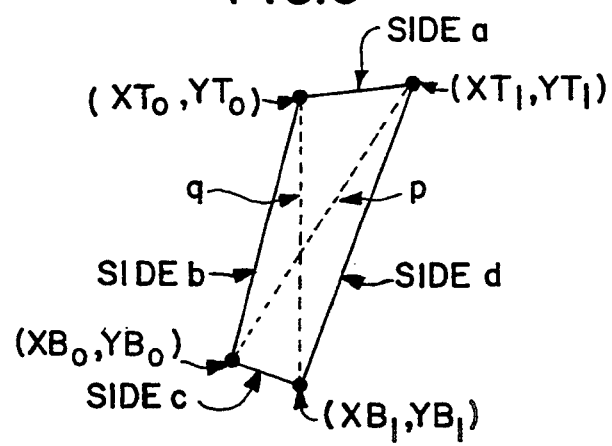
FIG. 6 is a diagrammatic illustration of a planar quadrilateral and the geometric coordinate information relating to a quadrilateral.
Figure 7:
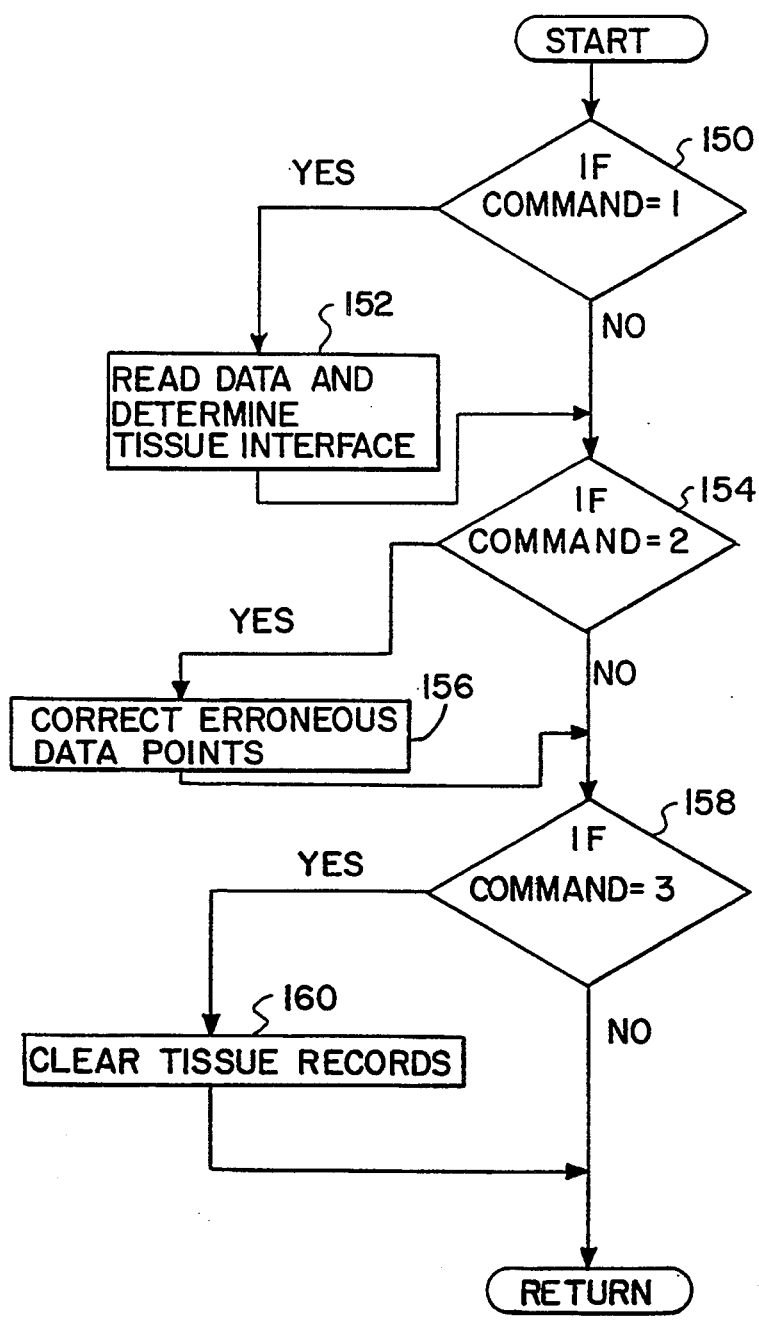
FIG. 7 is a generalized flow chart for software executed by the computer 14 which determines tissue interface boundaries and corrects erroneous scan data.

Referring now to FIG. 6, a quadrilateral is shown with the four sides, diagonals and intersection points of the sides labeled for convenience. In accordance therewith, the following formulas are used to determine the area contained within a particular quadrilateral. The points which are known defining the various quadrilaterals which make up the main longissimus muscle area 92b (the PK3 and PK4 points determined during scanning) are used to define quadrilaterals whose areas summed together define the total area of the main longissimus muscle 92b with high precision.

$$\text{Quadrilateral area} = (1/4) \sqrt{4pq - (b + d - a - c)^2} ,$$

where
$p = (XT_1 - XB_0)^2 + (YT_1 - YB_0)^2$,
$q = (XT_0 - XB_1)^2 + (YT_0 - YB_1)^2$,
$a = (XT_0 - XT_1)^2 + (YT_0 - YT_1)^2$,
$b = (XT_0 - XB_0)^2 + (YT_0 - YB_0)^2$,
$c = (XB_0 - XB_1)^2 + (YB_0 - YB_1)^2$, and
$d = (XT_1 - XB_1)^2 + (YT_1 - YB_1)^2$ Referring now to FIG. 7, a flow chart for the program executed by computer 14 which determines tissue interface locations and corrects erroneous data to provide an accurate measurement of fat thickness and longissimus muscle area according to the present invention is shown. At step 150, if the command received by the program is a 1, then program execution continues at step 152 where the program reads the data from the instrument 12 to determine tissue interface locations. After step 152 program execution continues at step 154. If the answer to the inquiry at step 150 is no, program execution continues with step 154. At step 154, if the command received is 2, then at step 156 the interface locations for certain scans are analyzed and erroneous data or artifacts are corrected. If at step 154 the command is not 2 then program execution continues with step 158. If at step 158 the command received is a 3, then the tissue records are cleared from memory at step 160.

Figure 8:
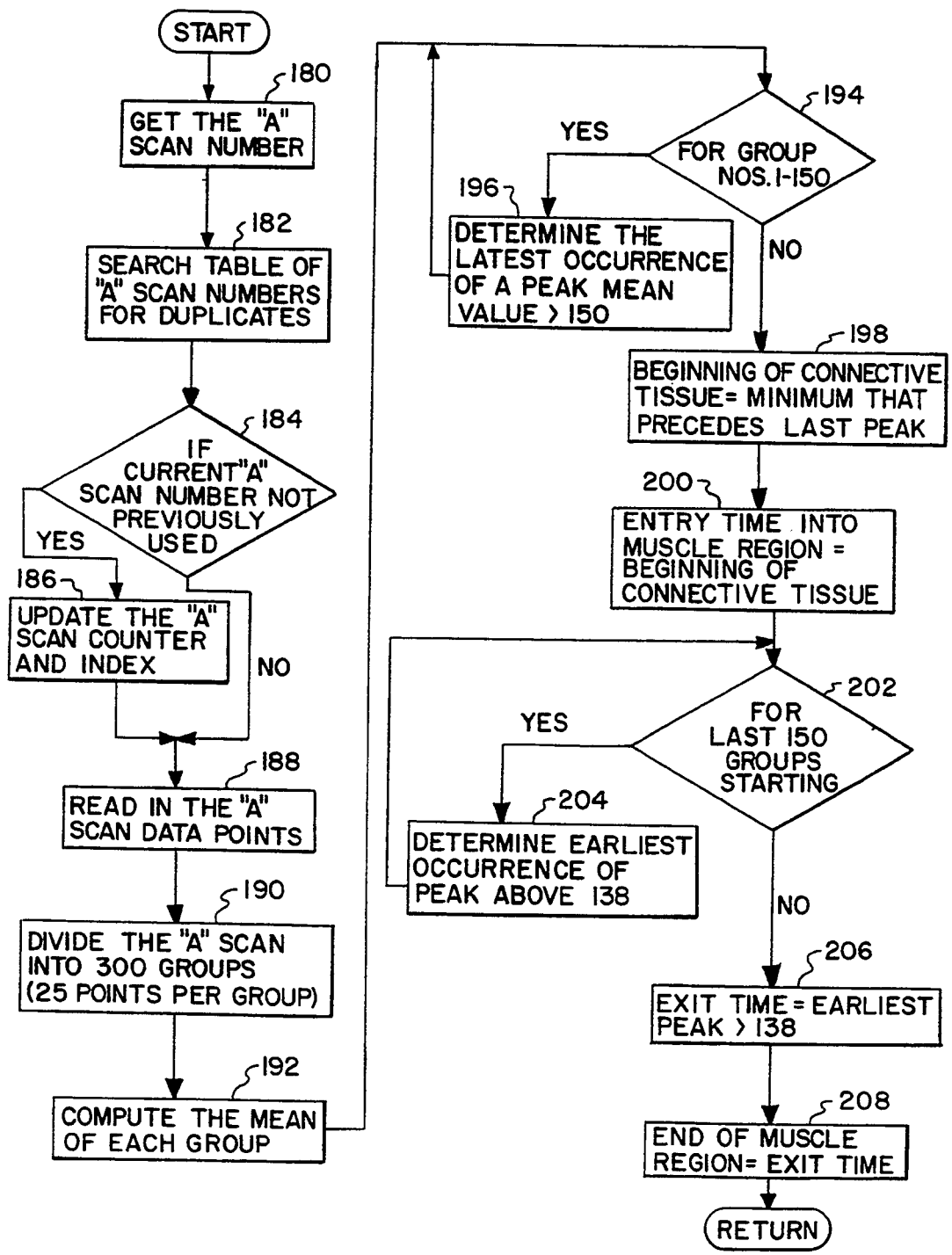
FIG. 8 is a more detailed flow chart of the "read data and determine tissue interfaces" step of FIG. 7.

Referring now to FIG. 8, a more detailed flow chart for the read data and determine tissue interfaces of step 152 of FIG. 7 is shown. The approach taken in the software is to determine the location of the back of the rib or loin and work towards the location of the transducer in determining the tissue interface locations. The data received from instrument 12 by computer 14 includes a scan number which is a serialized number attached to and incremented with each group of data bytes defining a scan, wherein each of the digitized scans includes approximately 8,000 bytes of data. At step 180 in FIG. 8, the scan number or A scan number is obtained, and the table of A scan numbers is searched for duplicates at step 182. Following step 182, at step 184, if the current A scan number is a number that has not been previously used for a recent scan already received, then the A scan counter and index is updated at step 186 after step 184. If the test at step 184 is false, then program execution continues with step 188. Program execution continues at step 188 following step 186 also. At step 188, the A scan data points corresponding to the A scan number obtained in step 180 are read in over the IEEE 488 interface 30 by computer 14. Subsequently at step 190 the A scan data is divided into approximately 300 groups of 25 data points per group. Next, for each group determined in step 190 a mean is calculated at step 192. Next at steps 194 and 196, a loop is executed for the groups of data numbered 1 through 150 to determine the last occurrence of a peak mean value above 150 (or any other predetermined peak value). Subsequently at step 198, the beginning of the connective tissue is determined to be the minimum that precedes the last peak greater than 150 detected in the loop of steps 194 and 196. Following step 198, the entry time into the muscle region is determined to be the beginning of the connective tissue at step 200. After step 200, a loop is executed at steps 202 and 204 for the last 150 data groups which are comprised of 25 points per group, to determine the earliest occurrence of a peak above a predetermined value or 138 at step 204. The loop of steps 202 and 204 executes 150 times with the last 150 groups of data. After the 150th execution of the loop, program execution continues at step 206 wherein the exit time i.e. the time at which the signal crosses the back of the muscle is determined to be the earliest peak which is greater than 138. Next at step 208, the end of the muscle region is set equal to the exit time which is the point in time at which the earliest peak above 138 was detected at step 206. Subsequently a return is executed to the calling routine.

Figure 9:
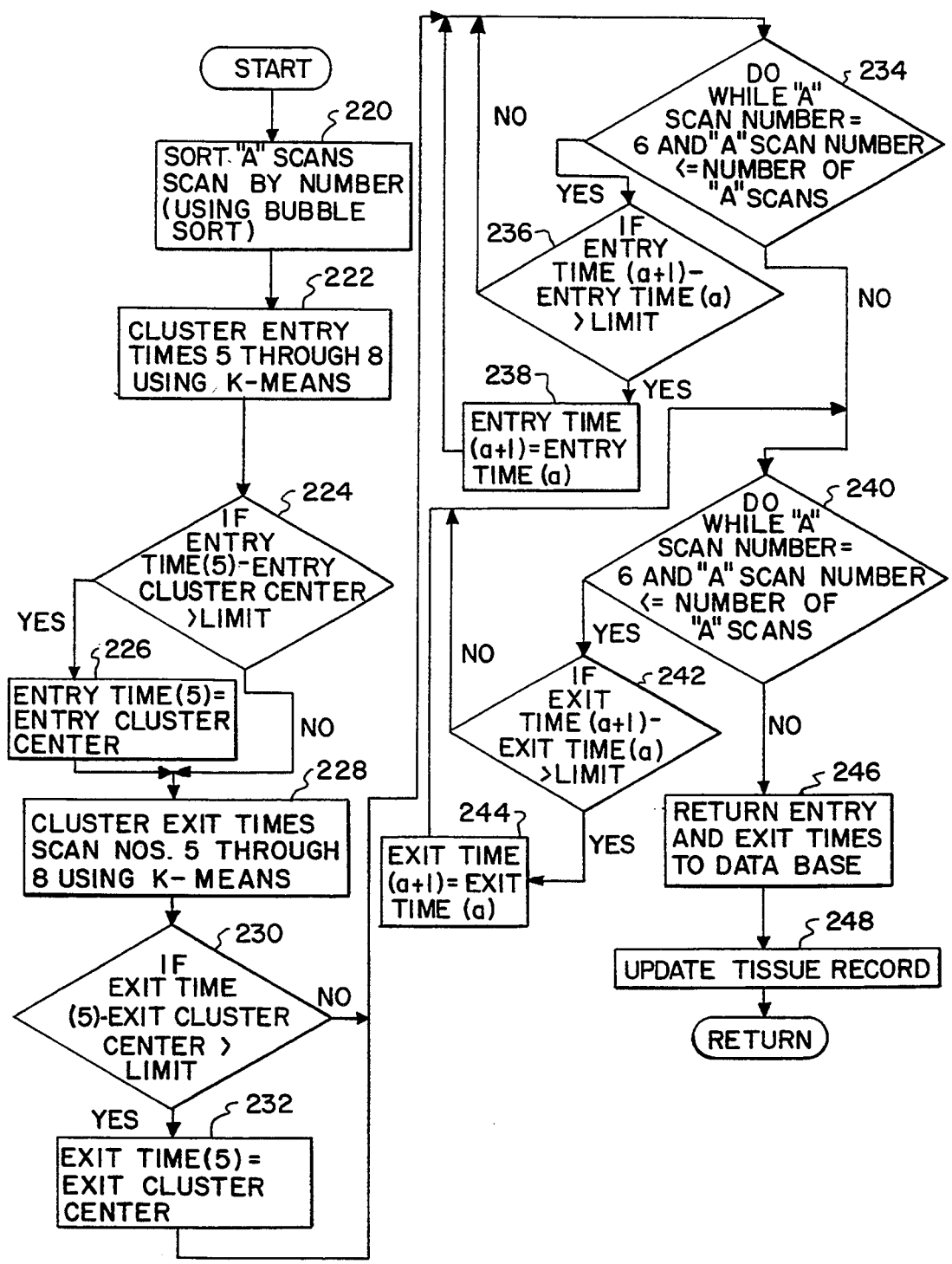
FIG. 9 is a more detailed flow chart of the "correct erroneous data points" step of FIG. 7.
Figure 16:
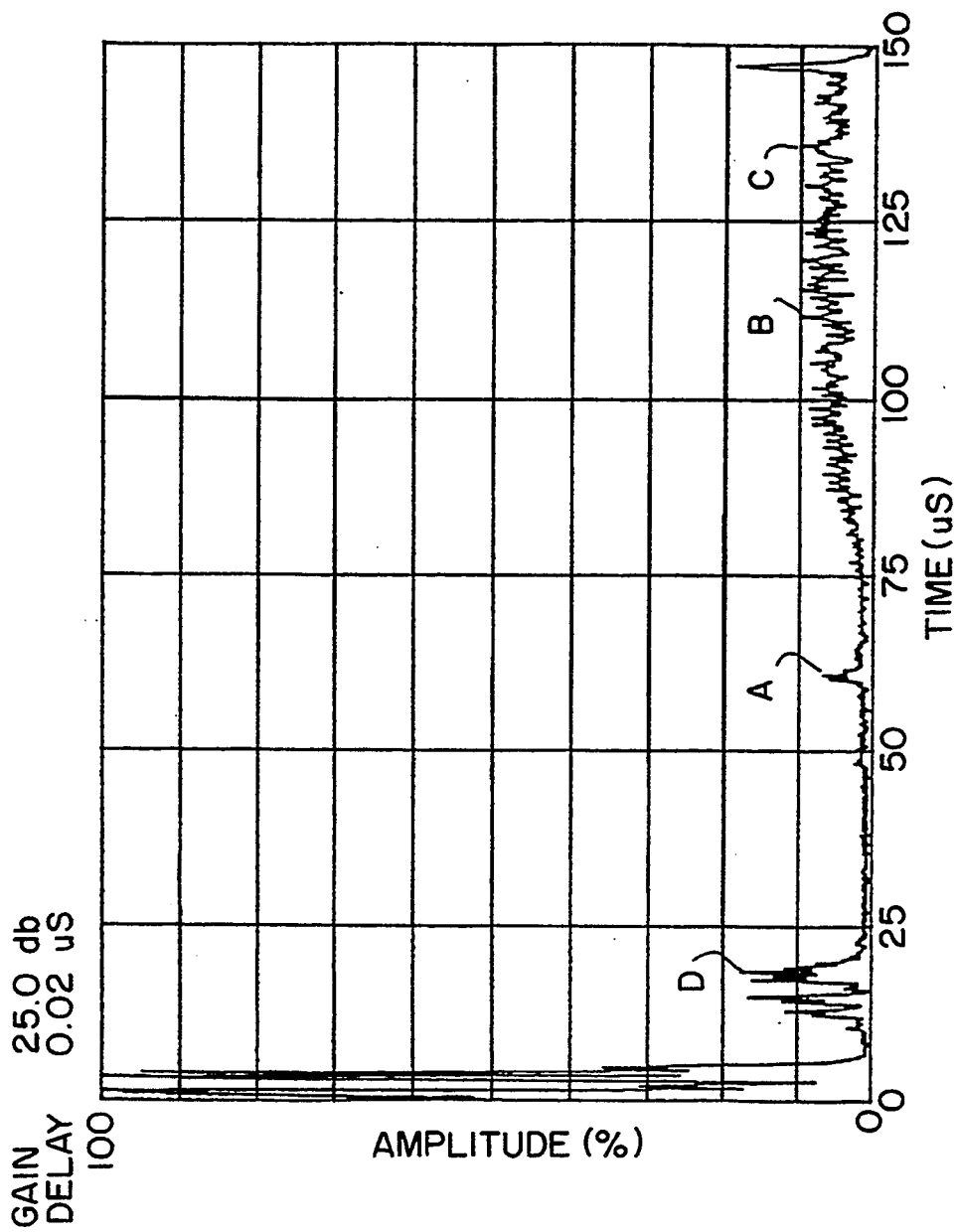
FIG. 16 is a chart depicting the electronic "full video" signal produced by the instrument 12 at a location 5 inches from the midline of pork (live or carcass).
Figure 16A:
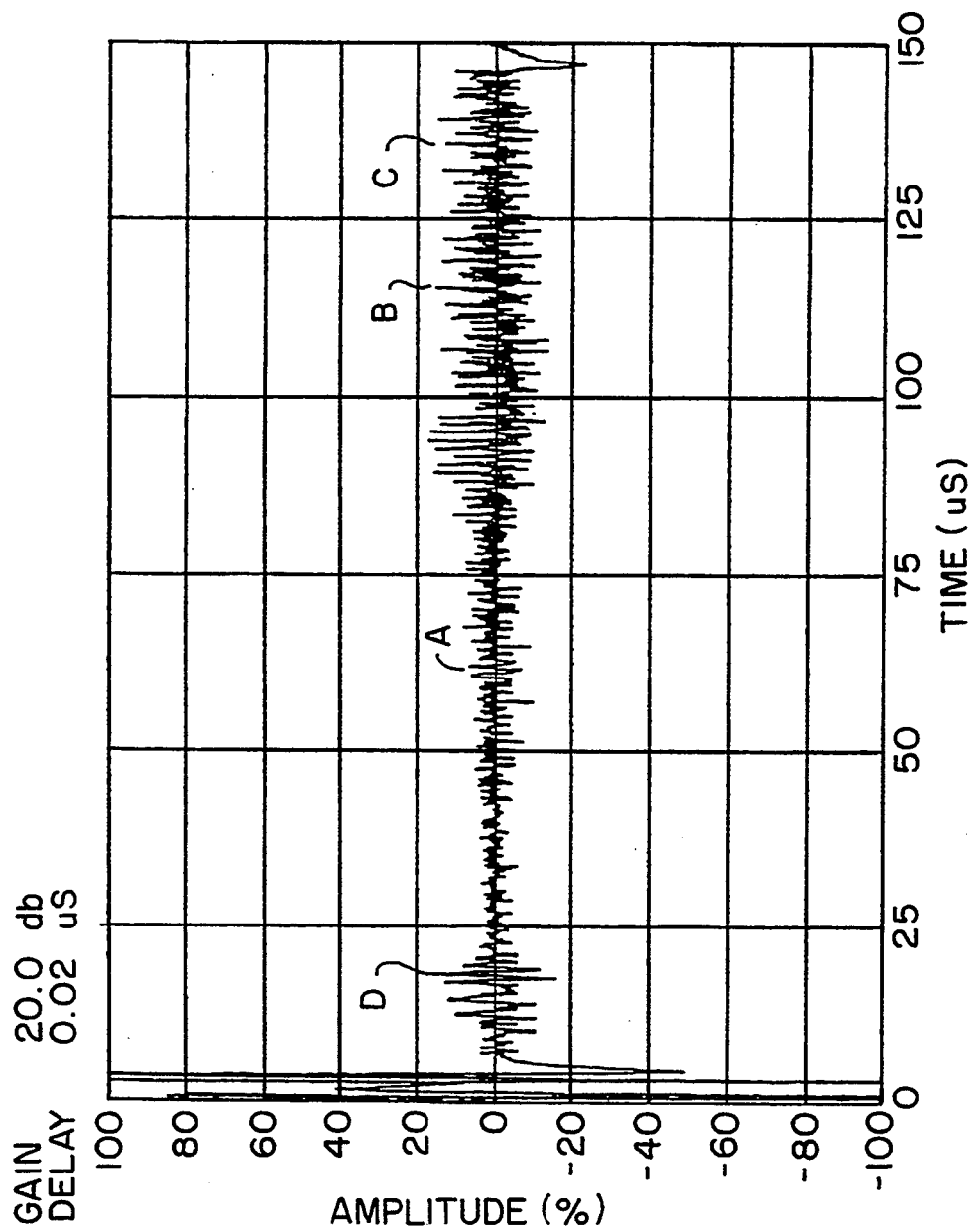
FIG. 16A is a chart depicting the electronic "RF" signal corresponding to FIG. 16 produced by the instrument 12 at a location 3 inches from the midline of pork (live or carcass).

Referring now to FIG. 9, a more detailed flow chart for the "correct erroneous data points" step 156 of FIG. 8 is shown. Artifacts and data readings out of reasonable limits are corrected by this routine. For example, if location B of FIG. 16 is not properly located by the software algorithm of FIGS. 8 or 10, then adjacent scan data (from FIG. 15 as an examplary adjacent scan) is used to establish an adjusted or corrected location for location B in FIG. 16. At step 220, the total A scans which have been stored are sorted by scan number using a bubble sort routine well known to those skilled in the art of programming. Next at step 222, a cluster value is determined for the "entry times" corresponding to scan number 5 through scan number 8 using a "K-means" routine which is well known to those skilled in the art. In particular, the K-means routine will provide a center value for a cluster of points in an X-Y coordinate plane. Thus, a center value is calculated for the entry times determined in scans numbered 5 through 8 using the routine in step 222. Subsequently in step 224 if the "entry time" for scan 5 minus the "entry cluster center value" is greater than a predetermined limit then the "entry time" for scan 5 is set equal to the "entry cluster center value" at step 226. If the conditional at step 224 is not satisfied then program execution continues with step 228. Next, at step 228 the "exit times" for scan numbers 5 through 8 are clustered using the "K-means" algorithm as was done in step 222 for the entry times. Subsequently at step 230 if the "exit time" for scan number 5 minus the "exit cluster center value" calculated at step 228 is greater than the predetermined limit of step 224 then the "exit time" for scan number 5 is set equal to the "exit cluster center value" at step 232. If the result for the conditional in step 230 is "no" then program execution continues at step 234. At step 234 a do-while loop including steps 236 and 238 is executed while the A scan number is equal to 6 and less than or equal to the total number of A scans received from the instrument 12. At step 236 if the entry time for the next A scan minus the entry time for the present A scan is greater than a predetermined limit then the entry time for the next A scan is set equal to the entry time of the present A scan. The counter "a" is a counter for establishing the subscript in steps 236 and 238 corresponding to the scan number of interest determined in step 234. The scan number is incremented each time through the loop of step 234 and 236 so that all adjacent scan entry times are compared with one another. If at any time the condition in step 236 is satisfied, then the entry time for the next scan is set equal to the entry time for the present scan number. Once scan numbers 6 through the last scan number have been processed in the do-while loop of step 234, then program execution will continue with step 240 wherein a do while loop consisting of steps 242 and 244 perform a similar task as steps 234 through 238 with regard to the exit times for adjacent scans in the scans numbered 6 through the last scan. At step 242 if the exit time for the next adjacent scan minus the exit time for the present scan is greater than a predetermined limit then the exit time for the next scan is set equal to the exit time for the present scan at step 244. After step 244 program execution returns to step 240 where the do-while loop causes the scan number to increment by 1 until the last scan number is encountered. When the last scan number is encountered at step 240 then program execution continues with step 246 wherein the entry and exit times which are determined and revised by this routine are returned to the database, and the tissue records are updated at step 248. Program execution then returns to the calling routine.

Figure 10:
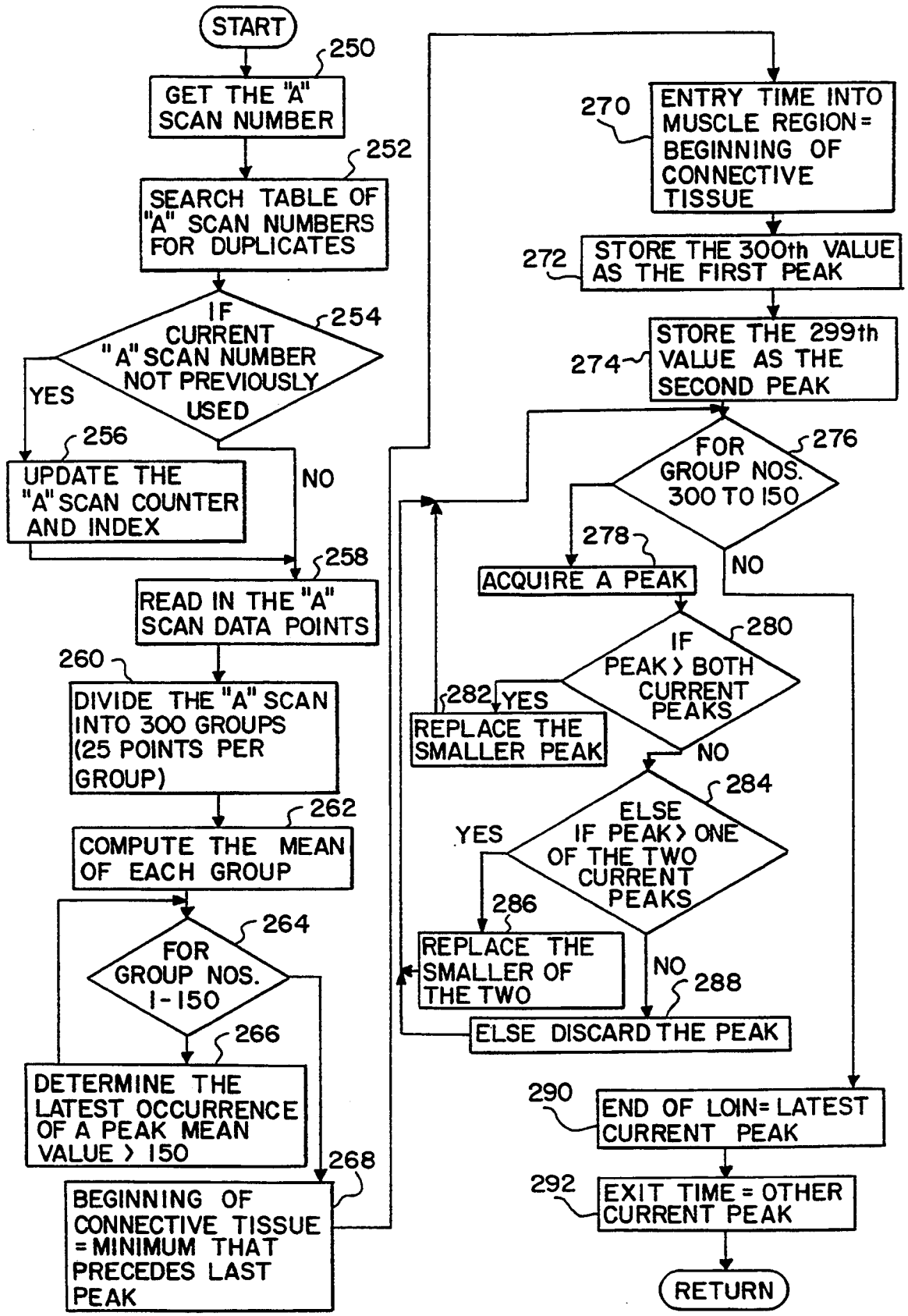
FIG. 10 is a flow chart of an alternate embodiment of the "read data and determine tissue interfaces" step of FIG. 7.

Referring now to FIG. 10, an alternate embodiment for step 152 "read data and determine tissue interfaces" of FIG. 7 is shown. In this embodiment, the tissue interface locations or coordinates are determined according to an alternate algorithm. At step 250 the A scan number is requested from instrument 12 over the IEEE 488 interface 30 by the computer 14. Instrument 12 responds with a scan number. At step 252 the computer 14 searches the table of A scan numbers in memory for duplicates. At step 254 if the current A scan number has not been previously used, then step 256 is executed and the A scan counter is updated as well as an index counter in memory. If at step 254 the A scan number is not previously used, then program execution continues at step 258 wherein the computer 14 reads in the A scan data points from instrument 12 over the IEEE 488 interface 30. Subsequently at step 260 the A scan data is divided into 300 groups consisting of 25 points per group. Next, at step 262, the mean value of each group determined in step 260 is calculated. Thereafter at steps 264 and 266, for group numbers 1 through 150, the latest occurrence of a peak mean value greater than 150 is determined. After the loop of steps 264 and 266 has fully executed for group numbers 1 through 150, then step 268 executes next. At step 268, the beginning of the connective tissue is determined in accordance with the time of occurrence of the group mean value determined for group numbers 1 through 150, which is the minimum mean value that first precedes the last peak determined in step 266. Next at step 270 the entry time into the muscle region is set equal to the beginning of the connective tissue time determined in step 268. Next at step 272, the 300th mean value is stored as the first peak value. Subsequently at step 274 the 299th group mean value is stored as the second peak value. After step 274, a loop consisting of steps 276 through step 288 executes for group numbers starting with 300 and working the loop counter increment value down to group number 150. At step 278 a current group mean value is compared with adjacent mean values to determine whether or not a peak is present or has been determined. Once a peak is acquired or found at step 278, then at step 280 the peak is compared with the peak values from steps 272 and 274. If the peak is greater than both current peaks then step 282 executes and the smaller peak is replaced with the peak acquired in step 278. If the conditional at step 280 is not satisfied then step 284 is executed wherein if the peak acquired in step 278 is greater than one of the two current peaks then step 286 executes and the smaller of the two peaks determined in step 272 and step 274 are replaced by the peak acquired in step 278. If the conditional in step 284 is not satisfied, then the peak acquired in step 278 is discarded in step 288. Program execution continues at step 276 following steps 282, 286 and 288. The loop consisting of steps 276 through 288 will execute for group numbers 300 down to 150. Program execution then continues with step 290 wherein the "end of the rib/loin" time period is determined according to the position of the latest current peak in the group of mean values calculated for the data. The position of this value corresponds to a time of flight of the ultrasonic signal, and thus corresponds directly with the thickness of the muscle or fat region which has been determined in accordance with the end of the rib/loin tissue interface location. After step 292, the exit time is determined in accordance with the other current peak or the second peak value which results from the loop of steps 276 through 288. After step 292, program execution returns to the calling routine.

Referring now to FIG. 11, an enlarged partial view of the transducer 36 with the rubber boot 38 installed over the transducer/couplant manifold assembly is shown. Water or other couplant supplied to the couplant manifold 80 via hose 40 is supplied internally through manifold 80 into the void 94 and fills void 94 so that a coupling fluid is present between transducer 36 and the live animal or carcass 92. The lip 38a of the cylindrical boot 38 provides a fluid seal with the live animal or carcass when slight pressure is applied downward on the boot by the spring 86 shown in FIG. 3a. Ring 80a of couplant manifold 80 provides an enlarged diameter area wherein a fluid seal is formed with boot 38 to define the void or chamber 94 and maintain water therein.

Referring now to FIGS. 12-16 and FIGS. 12A-16A, "full video" and corresponding "RF" ultrasound signals produced by the instrument 12 and digitized for subsequent analysis by computer 14 for locations 1 inch through 5 inches away from the midline are respectively shown. In each of the graphical representations of the signals, the front of the longissimus muscle is indicated by the letter A and the rear of the longissimus muscle is indicated by the letter B. In addition, the back of the rib/loin is represented by the peak at locations C. Finally, an interface between the first and second fat layers is indicated at locations D. These peaks or tissue interface locations are the primary location indicators used by the device 10 in determining tissue interface locations and calculating tissue thicknesses and longissimus muscle areas. It is not uncommon for a third fat layer to be present in the live animal or carcass and normally that layer is evidenced by a peak at location E. However, in the present figure, that third fat layer is not present and the peak does not appear. Additionally, the most important interface boundaries that are detected are the A and B locations which define the front and rear of the longissimus muscle. These points are crucial in determining the area of the muscle with high accuracy.

Figure 17:
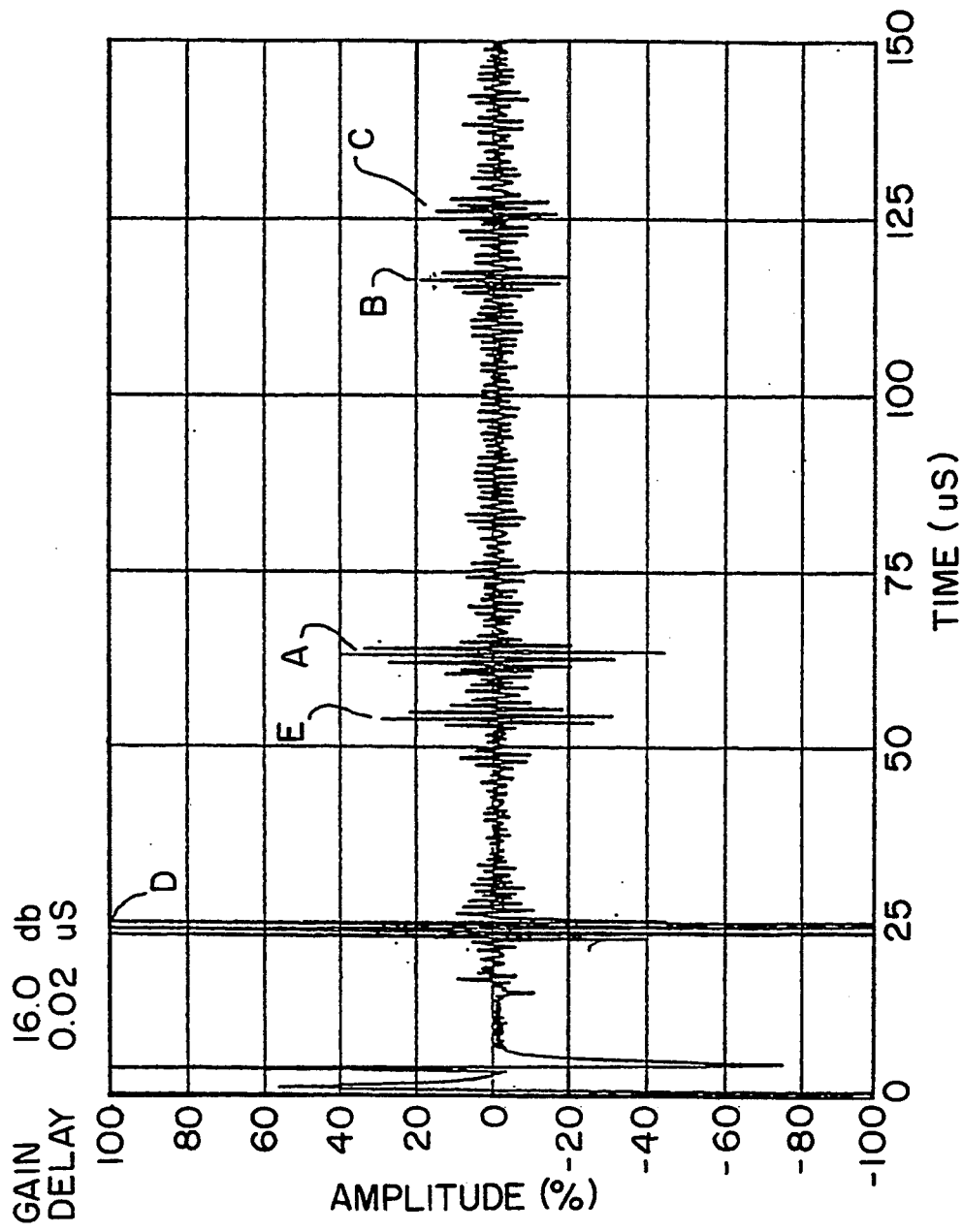
FIG. 17 is a typical chart depicting an electronic "RF" ultrasonic signal produced by instrument 12 for a pork (live or carcass) having a third fat layer.

Referring now to FIG. 17, an RF scan produced by instrument 12 for a live pork or pork carcass is shown. The tissue interface boundaries are more easily located in this graphical depiction as a result of refinements in the calibration and setup of the device 10. Locations A and B define the longissimus muscle boundaries. Location C is the back of the rib/loin. Location D is the interface between the first and second fat layers. Further, location E is the interface between the second and third fat layers. FIG. 17 is one example of the additional fat layer which is occasionally present and detected. It should be noted that an RF or Full Video scan signal is identical for a live pork or corresponding carcass.

Figure 18:
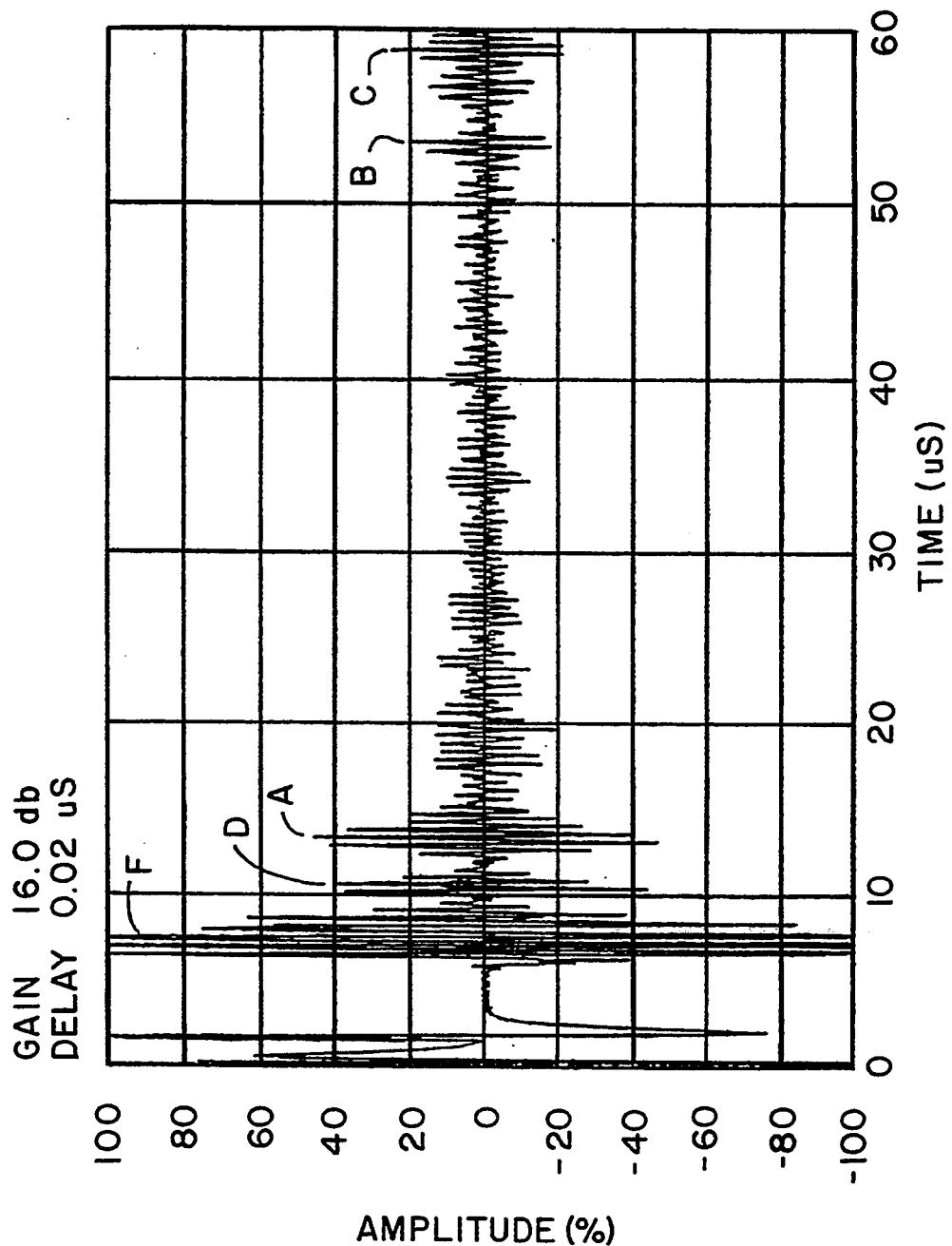
FIG. 18 is a typical chart depicting an electronic "RF" ultrasonic signal produced by instrument 12 for a beef (live or carcass).

Referring now to FIG. 18, an RF scan produced by instrument 12 for a live beef or beef carcass is shown. The tissue interface boundaries are more easily located in this graphical depiction as a result of refinements in the calibration and setup of the device 10. Locations A and B define the longissimus muscle boundaries. Location C is the back of the rib/loin. Location D is the interface between the first and second fat layers. Location F is the interface between the animal hide and the first fat layer. It should be noted that an RF or Full Video scan signal is identical for a live beef or corresponding carcass.

An alternate approach utilizing multiple transducers arranged in a plane would produce a similar result as device 10. Analog multiplexers would switch each transducer to the instrument 12 to produce the multiple scans necessary for full analysis of the animal or carcass. With a multiple transducer approach, motors and position feedback hardware would not be needed.

A 8-page listing of the software corresponding to the flow chart of FIG. 8 is included after the end of the Description of The Preferred Embodiment and is titled ALG__Interfaces.C. In addition, a 2-page listing of a program written in the programming language C for the K-means calculation routine is also included.

In view of the description of the present invention and its capability to accurately determine fat thickness and loin eye area, it is believed that improved correlation with actual lean content is achieved as compared with prior art systems which use estimates of area and fat thickness.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

```
/* Alg_Interfaces.c*/

/*
***********************************************************************
* This is the function called by the main routine to determine the    *
* boundaries between fat and muscle, and the A-scan amplitudes at these *
* points. The results are written to the the global structure typedef *
* Working_Var.                                                         *
* Calling parameters: int cmd where                                    *
*                     1 - a valid A Scan with more to follow           *
*                     2 - No A Scans to follow                         *
*                     3 - Abort scan; disregrd data                    *
*                                                                      *
*                     Working_Var *wvp, a pointer to the global        *
*                                   structure of working variables     *
*                                                                      *
*                     Tbl_Typ *p, a pointer to a structure that        *
*                                 includes an array of 50 time         *
*                                 and amplitude values and the         *
*                                 number of a scans.                   *
*                                                                      *
*                     function returns 0 if OK                         *
*                                      any other integer if not OK     *
*                                                                      *
*                                                                      *
* *********************************************************************
*/ include <stdio.h>
include <math.h>
#include <string.h>
#include "workval.h"
include <conio.h> define BUFSIZE 1
define PREAMBLE 108
#define NUM_PTS 25
#define TOTAL_GROUPS 300
#define LIMIT 5
#define E_OK 0
#define ENTRY_PK 150
#define NTHRESH 138
#define XTHRESH 132
#define MAX_STRUCT 50
#define TRUE 1
#define FALSE 0
#define CASE_ZERO 0
define DIV_2 2.0 int  Alg_Interfaces(int cmd, Working_Var *wvp, Tbl_Typ *p)
{
FILE *ifp1;

extern float k_mean(float ctr1, float ctr2, float ctr3, float ctr4);
extern int Sav_New_Tissue_Rec(Working_Var *wvp);
extern int Delete_Tissue_Rec(Working_Var *wvp);
```

```c
char buf1[PREAMBLE]; /* input character buffer */
int i, j, k; /* loop counters */
unsigned char var3; /* digitizer A-scan data */
int point_value[NUM_PTS]; /* the array of point values */
float ex_val[TOTAL_GROUPS]; /* expected value of the group */
static int a_scan_count = 0; /* A Scan totalizer */
static int a_scan_index = 0; /* A Scan array index */
double variance[TOTAL_GROUPS]; /* the variance of the group of points */
static int l; /* A Scan number */
int status; /* inspection status , ok or fail */
float var1, var2; /* clustering values */
float ctr1, ctr2, ctr3, ctr4; /* values to be clustered */
float curr_value, prev_value; /* current and previous mean values */
int flag, end_flag; /* peak capture flags */
float end_prev_value; /* end peak previous value */
float var4, var5, var6, var7; /*temporary amplitude & tof values */
int tissue_rec_status; /* tissue record empty or full */
int sorted = FALSE; /* bubble sorted flag */
int count_flag; /* a scan counter flag */
char ch1; /* input test character */

/* temporary values used during sort */
float temp_exit_amp, temp_exit_time, temp_entry_amp, temp_entry_time;
int temp_scan_num;

typedef struct{   /* time and amplitude of a peak */
    float time;
    float value;
}PEAK1;

/* structures of peak values */
PEAK1 curr_peak;
PEAK1 latest_peak;
PEAK1 end_curr_peak;
PEAK1 end_latest_peak;

/* get A Scan number */
l = (int)wvp->WAscanNumber;

/* check for duplicate scan numbers */
i = 0;
count_flag = FALSE;

while((i < a_scan_count)&&(count_flag == FALSE)){
    if (p->Tbl[a_scan_count].scan_num == l)
       count_flag = TRUE;
    i++;
}
if ((count_flag == FALSE) && (cmd == 1)){
    a_scan_count++;
    a_scan_index = a_scan_count - 1;
}

/* assign file names */
ifp1 = fopen(wvp->WAscanFilename, "rb");

/* read in the A-scan identification data */
fread (buf1, PREAMBLE, 1, ifp1);

/* initialize the expected value and variance arrays */
for (k = 0; k < TOTAL_GROUPS; k++){
    ex_val[k] = 0.0;
}

/* read in the groups of data and compute expected value */
for (i = 0; i < TOTAL_GROUPS; i++){
    for (j = 0; j < NUM_PTS; j++){
        fread (&var3, BUFSIZE, 1, ifp1);
```

```
        if (var3 < 127)
            var3 = 254 - var3;
        point_value[j] = var3;
        ex_val[i] = ((float)point_value[j] + ex_val[i]);
    }
    ex_val[i] /= (float)NUM_PTS;

} /* end of "300" loop */

/* close the file */
fclose (ifp1);

/* scan the 300 points and select boundaries */
/* initialize the peak values */
curr_peak.value = 0.0;
curr_peak.time = 0;
latest_peak.value = 0.0;
latest_peak.time = 0;
end_curr_peak.value = 0.0;
end_curr_peak.time = 0;
end_latest_peak.value = 0.0;
end_latest_peak.time = 0;
prev_value = 0.0;
end_prev_value = 0.0;
flag = 0;
end_flag = 0;

/* survey the first 150 groups and record the time of the */
/* latest peak whose mean is greater than 150 */

/* update the peak value as successive values increase */
for (i = 0; i < 150; i++){
    if ((ex_val[i] > ENTRY_PK) && (ex_val[i] > prev_value)){
        curr_peak.value = ex_val[i];
        curr_peak.time = i;
        flag = 1; /* enable capture of latest peak */
    }
    /* retain the latest peak before values decline */
    if ((ex_val[i] < prev_value) && (flag == 1)){
        latest_peak.value = curr_peak.value;
        latest_peak.time = curr_peak.time;
        flag = 0; /* allows capture of only one peak */
    }
    /* update the previous value before returning to the */
    /* start of the loop */
        prev_value = ex_val[i];
}

/* move back from the latest peak to a minimum to include
all the connective tissue in the muscle region */
/* initialize variables for the while loop */
prev_value = latest_peak.value;
curr_value = 0.0;
i = latest_peak.time;
while ((prev_value > curr_value) || (prev_value >= NTHRESH)){
    prev_value = ex_val[i];
    i--;
    curr_value = ex_val[i];
}

/* add the entry data for the latest A Scan */
var4 = curr_value;
var5 = (float)(--i);

/* prepare to detect the end of loin eye */
/* examine 150 mean values starting with the last and move */
/* toward the center */
/* the amplitude threshold is 138 */
```

```
    for (i = 299; i > 180; i--){
       if ((ex_val[i] > XTHRESH) && (ex_val[i] > end_prev_value)){
          end_curr_peak.value = ex_val[i];
          end_curr_peak.time = i;
          end_flag = 1; /* enable capture of latest peak */
       }
       /* update the latest peak when values decline */
       if ((ex_val[i] < end_prev_value) && (end_flag == 1)){
          end_latest_peak.value = end_curr_peak.value;
          end_latest_peak.time = end_curr_peak.time;
          end_flag = 0; /* allows capture of only one peak */

}
       end_prev_value = ex_val[i]; /* update previous value */
    } var6 = end_latest_peak.value;
    var7 = end_latest_peak.time;

/* if A Scan is  valid put data in temporary storage for
       later review */
    if (cmd == 1){
       p->Tbl[a_scan_index].entry_amp = var4;
       p->Tbl[a_scan_index].entry_time = var5/DIV_2;
       p->Tbl[a_scan_index].exit_amp = var6;
       p->Tbl[a_scan_index].exit_time = var7/DIV_2;
       p->Tbl[a_scan_index].scan_num = 1;
/*     printf("\n%d %.2f %.2f", 1,p->Tbl[a_scan_index].entry_time,
                                  p->Tbl[a_scan_index].exit_time); */
       status = 0;
    } i = 0;
    do{
       printf("\n%d %.2f %.2f", 1,p->Tbl[i].entry_time,
                                  p->Tbl[i].exit_time);
       i++;
    } while (i < 20);

ch1 = getch();
    ch1++;

for (i = 20; i < a_scan_count; i++)
       printf("\n%d %.2f %.2f", 1,p->Tbl[i].entry_time,
                                  p->Tbl[i].exit_time);

if (cmd == 2){

/* sort the A-Scan data by A-Scan number */
       while (! sorted){
          sorted = TRUE;
          for (j = 0; j < a_scan_count -1; j++){
             if (p->Tbl[j].scan_num > p->Tbl[j+1].scan_num){
                sorted = FALSE;
                temp_scan_num = p->Tbl[j].scan_num;
                temp_exit_amp = p->Tbl[j].exit_amp;
                temp_exit_time = p->Tbl[j].exit_time;
                temp_entry_amp = p->Tbl[j].entry_time;
                temp_entry_time = p->Tbl[j].entry_time;

p->Tbl[j].scan_num = p->Tbl[j+1].scan_num;
                p->Tbl[j].exit_amp = p->Tbl[j+1].exit_amp;
                p->Tbl[j].exit_time = p->Tbl[j+1].exit_time;
                p->Tbl[j].entry_amp = p->Tbl[j+1].entry_amp;
                p->Tbl[j].entry_time = p->Tbl[j+1].entry_time;

p->Tbl[j+1].scan_num = temp_scan_num;
                p->Tbl[j+1].exit_amp = temp_exit_amp;
                p->Tbl[j+1].exit_time = temp_exit_time;
```

```
            p->Tbl[j+1].entry_time = temp_entry_amp;
            p->Tbl[j+1].entry_time = temp_entry_time;
        }
    }
}

/* cluster start times 5 through 8 */
ctr1 = p->Tbl[5].entry_time;
ctr2 = p->Tbl[6].entry_time;
ctr3 = p->Tbl[7].entry_time;
ctr4 = p->Tbl[8].entry_time;
var1 = k_mean(ctr1, ctr2, ctr3, ctr4);
/* var1 is the start times cluster center */

/* cluster end times 5 through 8 */
ctr1 = p->Tbl[5].exit_time;
ctr2 = p->Tbl[6].exit_time;
ctr3 = p->Tbl[7].exit_time;
ctr4 = p->Tbl[8].exit_time;
var2 = k_mean(ctr1, ctr2, ctr3, ctr4);
/* var2 is the end times cluster center */ printf("\n%.2f %.2f",var1,var2);

/* interpolate entry points if necessary */
for(i = 6; i < a_scan_count - 4; i++){
    /* compare a point to its preceding neighbor */
    if (fabs(p->Tbl[i].entry_time - p->Tbl[i-1].entry_time) > LIMIT)
        p->Tbl[i].entry_time = p->Tbl[i-1].entry_time;
}

/* interpolate exit points if necessary */
for(i = 6; i < a_scan_count - 4; i++){
    /* compare point to its preceding neighbor */
    if (fabs(p->Tbl[i].exit_time - p->Tbl[i-1].exit_time) > LIMIT)
        p->Tbl[i].exit_time = p->Tbl[i-1].exit_time;
} i = 0;
do{
    printf("\n%d %.2f %.2f", l,p->Tbl[i].entry_time,
                               p->Tbl[i].exit_time);
    i++;
} while (i < 20);

ch1 = getch();
for (i = 20; i < a_scan_count; i++)
    printf("\n%d %.2f %.2f", l,p->Tbl[i].entry_time,
                               p->Tbl[i].exit_time);

/* send the altered values to back to the main structure */
for (i = 0; i < a_scan_count; i++){
    wvp->WEntryAmplitude = p->Tbl[i].entry_amp;
    wvp->WEntryTof = p->Tbl[i].entry_time;
    wvp->WExitAmplitude = p->Tbl[i].exit_amp;
    wvp->WExitTof = p->Tbl[i].exit_time;
    wvp->WAscanNumber = p->Tbl[i].scan_num;

/* update tissue record */
    tissue_rec_status = Sav_New_Tissue_Rec(wvp);
    status = tissue_rec_status;

/* if error is indicated, attempt to delete record */
    if(tissue_rec_status){
        tissue_rec_status = Delete_Tissue_Rec(wvp);
        if (tissue_rec_status){ /* if error persists, quit */
            status = tissue_rec_status;
            i = a_scan_count;
```

```
            }
            else{
                tissue_rec_status = Sav_New_Tissue_Rec(wvp);
                if (tissue_rec_status){ /* If error persists, quit */
                    status = tissue_rec_status;
                    i = a_scan_count;
                }
                else
                    status = tissue_rec_status;
            }
        }
    }
    p->Cnt = a_scan_count; /* return total a scan count */
    a_scan_count = 0;

} /* end of "if" clause for cmd = 2 */

/* clear the tissue records if scan has been cancelled */
if (cmd == 3){
    a_scan_count = 0;

/* set all Tof and Amplitudes to zero */
    wvp->WEntryAmplitude = 0.0;
    wvp->WEntryTof = 0.0;
    wvp->WExitAmplitude = 0.0;
    wvp->WExitTof = 0.0;

/* initialize Tof and Amplitude of all tissue records */
    for (i = 0; i < MAX_STRUCT; i++){
        wvp->WAscanNumber = i + 1;

tissue_rec_status = Delete_Tissue_Rec(wvp);
        if (tissue_rec_status){ /* if error, quit */
            status = tissue_rec_status;
            i = MAX_STRUCT;
        }
        else
            status = tissue_rec_status;
    }
} return status;
}
/* k_mean.c */
/* an implementation of the K Means algorithm for determining
two cluster centers of a group of points */ include <stdio.h>
include <stdlib.h>
#include <math.h>
define  CTR_OFFSET 10 float k_mean(float ctr1,float ctr2, float ctr3, float ctr4)
{ float bag1[5], bag2[5]; /* arrays to store data point clusters */
    float sumbag1, sumbag2; /* sum of points in a cluster */
    float center1, center2; /* initial cluster centers */
    float newcenter1, newcenter2; /* updated cluster centers */
    int bag1_num_items, bag2_num_items; /* number of items in the clusters */
    int i,k; /* counter index */
    int bag1_final_val, bag2_final_val; /* final cluster sizes */ typedef struct{     /* structure of data points */
        float peak_time;
        float peak_value;
    } points;
```

```c
points region[4]; /* array of structures of point data */

/* initialize the variables */
center1 = 0.0;
center2 = 0.0;
newcenter1 = ctr1;
newcenter2 = ctr2;
bag1_num_items = 0;
bag2_num_items = 0;
sumbag1 = 0.0;
sumbag2 = 0.0;

region[0].peak_time = ctr1;
region[1].peak_time = ctr2;
region[2].peak_time = ctr3;
region[3].peak_time = ctr4;

for (i = 0; i < 5; i++){
    bag1[i] = 0;
    bag2[i] = 0;
} do{
    center1 = newcenter1;
    center2 = newcenter2;
    for (i = 0; i < 4; i++){
        if (fabs(region[i].peak_time - center1) <
            fabs(region[i].peak_time - center2)){
            bag1[bag1_num_items] = region[i].peak_time;
            bag1_num_items++;
        }
        else{
            bag2[bag2_num_items] = region[i].peak_time;
            bag2_num_items++;
        }
    }

/* update center #1 */
    for (i = 0; i < bag1_num_items; i++)
        sumbag1 += bag1[i];
    if (bag1_num_items > 0)
        newcenter1 = sumbag1/(float)bag1_num_items;
    /* update center #2 */
    for (i = 0; i < bag2_num_items; i++)
        sumbag2 += bag2[i];
    if (bag2_num_items > 0)
        newcenter2 = sumbag2/(float)bag2_num_items;

/* reset variables for the next iteration */
    sumbag1 = 0.0;
    sumbag2 = 0.0;
    printf ("\n\n%d", bag1_num_items);
    printf ("\n%f", newcenter1);
    printf ("\n%d", bag2_num_items);
    printf ("\n%f", newcenter2);
    bag1_final_val = bag1_num_items;
    bag2_final_val = bag2_num_items;
    bag1_num_items = 0;
    bag2_num_items = 0;
    for (i = 0; i < 5; i++){
        bag1[i] = 0.0;
        bag2[i] = 0.0;
    }

} while ((center1 != newcenter1)||(center2 != newcenter2));

if(bag1_final_val > bag2_final_val)
    return newcenter1;
else
    return newcenter2;
}
```

What is claimed is:

1. A non-invasive device for grading a live animal or carcass, comprising:
   an ultrasonic pulser/receiver means for transmitting ultrasonic pulse signals and receiving reflected ultrasonic signals, said pulser/receiver means producing a plurality of ultrasound signals corresponding to said received reflected ultrasonic signals;
   drive means for automatically positioning said ultrasonic pulser/receiver means at a plurality of locations along a predetermined path and for urging said ultrasonic pulser/receiver means in contact with the animal or carcass, said drive means producing a position signal corresponding to the relative position of said ultrasonic pulser/receiver means with respect to a known reference location; and
   means for analyzing said ultrasound signals and said position signal to produce a leanness signal corresponding to the percentage lean content of the live animal or carcass.

2. The device of claim 1 wherein said predetermined path is defined by a curved member and said drive means includes a motor that transports said pulser/receiver means along said curved member, said drive means further including resilient moving means for resiliently moving said pulser/receiver means along a path substantially perpendicular to said curved member and encouraging contact between said animal and said pulser/receiver means, and wherein said position signal is comprised of a displacement signal corresponding to the relative distance said pulser/receiver means is displaced from said predetermined path and a path signal corresponding to the relative location of said pulser/receiver means along said predetermined path defined by said curved member.

3. The device of claim 2 wherein said means for analyzing includes a processor means having:
   (1) means for digitizing and storing a plurality of corresponding ones of said ultrasound signal, said displacement signal and said path signal;
   (2) means for determining muscle/fat tissue interface boundary locations in each of said ultrasound signals;
   (3) means for calculating muscle tissue area from said muscle/tissue interface boundary locations and corresponding ones of said displacement signals and said path signals and thereby producing said leanness signal.

4. The device of claim 3 wherein said muscle/fat tissue interface boundary locations in each ultrasound signal are determined according to the following algorithm:
   (1) dividing each digitized ultrasound signal into groups of data points;
   (2) computing a mean value for each of said groups of data points;
   (3) determining a muscle tissue entry time by analyzing the first half of said mean values to ascertain the latest occurrence of one of said mean values having a value in excess of a first predetermined peak limit; and
   (4) determining a muscle tissue exit time by establishing the last of said mean values as a first peak value and the second to last of said mean values as a second peak value and in reverse order comparing each of the latter half of said mean values with said first and second peak values, and if one of said mean values is greater than both said first and said second peak values then replace the smaller of said first and second peak values with said mean value, and if said mean value is greater than said first or said second peak value then replace the smaller of said first and second peak values with said mean value.

5. The device of claim 4 wherein adjacent ones of said muscle tissue entry times and said muscle tissue exit times, in conjunction with corresponding ones of said displacement signal and said path signal, define unique quadrilaterals whose summed areas defined the muscle area bounded thereby.

6. The device of claim 5 including a fluid manifold attached to said pulser/receiver means and which defines a fluid reservoir surrounding said pulser/receiver means when said ultrasonic pulser/receiver means is urged in contact with said animal or carcass, and wherein ultrasonic coupling fluid is supplied to said fluid manifold to maintain and maximize ultrasonic coupling between said animal or carcass and said ultrasonic pulser/receiver.

7. A non-invasive device for grading a live animal or carcass comprising:
   an ultrasonic transducer including means for emitting ultrasonic signals and means for detecting ultrasonic signal reflections and producing a corresponding ultrasound signal;
   means for supplying an excitation signal to said ultrasonic transducer, said means for supplying having an excitation input and responding to signals supplied to said excitation input producing said excitation signal;
   positioning means attached to said transducer, said positioning means including a position input, said positioning means disposed in close proximity to the live animal or carcass so that said ultrasonic transducer is ultrasonically coupled to the live animal or carcass, said positioning means moving said transducer relative to said live animal or carcass in response to signals supplied to said position input;
   encoder means coupled to said positioning means for providing a position feedback signal in accordance with the position of said positioning means; and
   processor means for monitoring said position feedback signal and supplying a position signal to said position input so that said positioning means moves said transducer to one of a plurality of predetermined positions adjacent the live animal or carcass, said processor means also monitoring said corresponding ultrasound signal and calculating the area of a longissimus muscle of the live animal or carcass and the thickness of fat layers adjacent the longissimus muscle at a predetermined rib/loin area cross-sectional location of said live animal or carcass.

8. The device of claim 7 wherein said positioning means moves said transducer along a predetermined path defined by a curved member, and including resilient means for urging said ultrasonic transducer in contact with said animal or carcass, said resilient means including a linear transducer means for producing a displacement signal corresponding to the relative movement of said transducer with respect to said predetermined path, and wherein said processor means receives said displacement signal and normalizes said ultrasonic signals in accordance with said displacement signal to ascertain the thickness of fat layers and the cross-sectional area of the longissimus muscle.

9. The device of claim 8 including a fluid manifold attached to said ultrasonic transducer and which defines a fluid reservoir surrounding said ultrasonic transducer when said ultrasonic transducer is urged in contact with said animal or carcass, and wherein ultrasonic coupling fluid is supplied to said fluid manifold to maintain and maximize ultrasonic coupling between said animal or carcass and said ultrasonic transducer.

10. A non-invasive device for grading a live animal or carcass comprising;
an ultrasonic transducer including means for emitting ultrasonic signals and means for detecting ultrasonic signal reflections and producing a corresponding ultrasound signal;
means for supplying an excitation signal to said ultrasonic transducer, said means for supplying having an excitation input and responding to signals supplied to said excitation input producing said excitation signal;
positioning means attached to said transducer, said positioning means including a position input, said positioning means disposed in close proximity to the live animal or carcass so that said ultrasonic transducer is ultrasonically coupled to the live animal or carcass, said positioning means moving said transducer relative to said live animal or carcass along a predetermined path defined by a curved member in response to signals supplied to said position input, and said positioning means also including resilient means for urging said ultrasonic transducer in contact with said animal or carcass, said resilient means including a linear transducer means for producing a displacement signal corresponding to the relative movement of said transducer with respect to said predetermined path;
encoder means coupled to said positioning means for providing a position feedback signal in accordance with the position of said positioning means; and
a fluid manifold attached to said ultrasonic transducer and which defines a fluid reservoir surrounding said ultrasonic transducer when said ultrasonic transducer is urged in contact with said animal or carcass, and wherein ultrasonic coupling fluid is supplied to said fluid manifold to maintain and maximize ultrasonic coupling between said animal or carcass and said ultrasonic transducer; and
processor means for monitoring said position feedback signal and supplying a position signal to said position input so that said positioning means moves said transducer to one of a plurality of predetermined positions adjacent the live animal or carcass, said processor means also monitoring said corresponding ultrasound signal and determining the area of a longissimus muscle of the live animal or carcass and the thickness of fat layers adjacent the longissimus muscle at a predetermined rib/loin area cross-sectional location of said live animal or carcass, wherein said processor means receives said displacement signal and normalizes said ultrasonic signals in accordance with said displacement signal to ascertain the thickness of fat layers and the cross-sectional area of the longissimus muscles, and wherein said processor means includes:
(1) means for digitizing and storing a plurality of said ultrasound signals and a corresponding one of said position feedback signal for each of said ultrasound signals stored;
(2) means for detecting peak signal values and determining muscle/fat tissue interface boundary locations from each of said stored ultrasound signals and producing an entry time value and an exit time value for each ultrasound signal thereby defining when each of said ultrasound signals entered and exited the longissimus muscle area;
(3) means for calculating longissimus muscle area from said entry time values, said exit time values and corresponding ones of said position feedback signals.

11. The device of claim 10 wherein said processor means is a computer having analog I/O, digital I/O, RAM, and ROM.

12. The device of claim 11 wherein said entry time values, said exit time values and said position feedback signals define a series of adjacent quadrilaterals whose sum equals longissimus muscle area.

13. The device of claim 12 including means for estimating the area of the ventral longissimus muscle and the dorsal longissimus muscle in view of the relative shape of the outermost ones of said quadrilaterals which define the area of the longissimus muscle.

14. A non-invasive method for grading a live animal or carcass, comprising the steps of:
providing an ultrasound unit which contacts the live animal or carcass at a predetermined location and which emits and receives ultrasonic signals and produces a reflection signal corresponding to received ultrasonic signals;
positioning said ultrasound unit in contact with the live animal or carcass at a predetermined location of the live animal or carcass;
moving said ultrasound unit along a predetermined path while maintaining contact between said ultrasound unit and the live animal or carcass;
providing a location feedback device mechanically connected to said ultrasound unit that produces a location feedback signal corresponding to the position of said ultrasound unit in relation to said predetermined path;
storing said reflection signal and said position signal at a plurality of locations along said predetermined path to produce a collection of stored reflection signals; and
analyzing said collection of stored reflection signals and said position signals and automatically calculating therefrom a lean content rating for the live animal or carcass.

15. The method of claim 14 including the steps of:
providing a curved member defining said predetermined path and corresponding to the curvature of the animal or carcass at a predetermined location of the animal or carcass;
providing a motorized device capable of moving along said curved member, said motorized device providing said location feedback signals corresponding to the location of said motorized device with respect to said curved member;
attaching said ultrasound unit to said motorized device;
energizing said motorized device to move said ultrasound unit along said predetermined path while simultaneously storing said reflection signals and said location feedback signal for each reflection signal.

16. The method of claim 15 wherein said analyzing step includes the steps of:
performing the following analysis steps for each reflection signal in said collection of stored reflection signals:
(1) digitizing said reflection signal to produce a plurality of digital data sets wherein each data set describes a particular reflection signal;
(2) dividing each data set into a predetermined number of groups of data points;
(3) computing a mean value for each of said groups of data points;
(4) determining an entry time corresponding to one of said mean values having a value greater than a first predetermined peak limit for the first half of said groups of data points;
(5) determining an exit time by establishing the last of said mean values as a first peak value and the second to last of said mean values as a second peak value and in reverse order comparing each of the latter half of said mean values with said first and second peak values, and if one of said mean values is greater than both said first and said second peak values then replace the smaller of said first and second peak values with said mean value, and if said mean value is greater than said first or said second peak value then replace the smaller of said first and second peak values with said mean value;
(6) determining the physical beginning location of the muscle region of the animal or carcass to be the location within the animal or carcass corresponding in time with said entry time;
(7) determining the physical ending location of the muscle region of the animal or carcass to be the location within the animal or carcass corresponding in time with said exit time; and
calculating a muscle area value based upon said entry times and said exit times determined for each reflection signal and based upon said location feedback signal which defines the location of said ultrasound unit with respect to the animal or carcass for each of said reflection signals.

17. A non-invasive method for grading a live animal or carcass, comprising the steps of:
providing an ultrasound unit which contacts the live animal or carcass at a predetermined location and which emits and receives ultrasonic signals and produces a reflection signal corresponding to received ultrasonic signals;
positioning said ultrasound unit in contact with the live animal or carcass at a predetermined location of the live animal or carcass;
moving said ultrasound unit along a predetermined path while maintaining contact between said ultrasound unit and the live animal or carcass;
providing a curved member defining said predetermined path and corresponding to the curvature of the animal or carcass at a predetermined location of the animal or carcass;
providing a motorized device capable of moving along said curved member, said motorized device providing location feedback signals corresponding to the location of said motorized device with respect to said curved member;
attaching said ultrasound unit to said motorized device;
energizing said motorized device to move said ultrasound unit along said predetermined path while simultaneously storing said reflection signals and a corresponding feedback signal for each reflection signal,
storing said reflection signal at a plurality of locations along said predetermined path to produce a collection of stored reflection signals;
analyzing said collection of stored reflection signals and determining therefrom a lean content rating for the live animal or carcass, said analyzing step including performing the following analysis steps for each reflection signal in said collection of stored reflection signals:
(1) digitizing said reflection signal to produce a plurality of digital data sets wherein each data set describes a particular reflection signal;
(2) dividing each data set into a predetermined number of groups of data points;
(3) computing a mean value for each of said groups of data points;
(4) determining an entry time corresponding to one of said mean values having a value greater than a first predetermined peak limit for the first half of said groups of data points;
(5) determining an exit time corresponding to one of said mean values having a value in excess of a second predetermined peak limit for the second half of said groups of data points;
(6) determining the physical beginning location of the muscle region of the animal or carcass to be the location within the animal or carcass corresponding in time with said entry time;
(7) determining the physical ending location of the muscle region of the animal or carcass to be the location within the animal or carcass corresponding in time with said exit time; and
calculating a muscle area value based upon said entry times and said exit times determined for each reflection signal and based upon said location feedback signal which defines the location of said ultrasound unit with respect to the animal or carcass for each of said reflection signals.

18. The method of claim 17 including the steps of:
determining polygonal shapes from said entry times and exit times for adjacent reflection signals and calculating the area of said polygons; and
summing the area of said polygons to determine a total muscle area.

19. The method of claim 18 wherein the animal or carcass muscle is the longissimus muscle and including the step of
estimating the area of the ventral longissimus muscle and the dorsal longissimus muscle to arrive at a total longissimus muscle area value.

20. A non-invasive device for grading a live animal or carcass, comprising:
an ultrasonic pulser/receiver means for transmitting ultrasonic pulse signals and receiving reflected ultrasonic signals, said pulser/receiver means producing a plurality of ultrasound signals corresponding to said received reflected ultrasonic signals;
drive means for positioning said ultrasonic pulser/receiver means along a predetermined path and in contact with the animal or carcass, said drive means producing a position signal corresponding to the relative position of said ultrasonic pulser/receiver with respect to the animal or carcass wherein said predetermined path is defined by a curved member and said drive means includes a motor that transports said pulser/receiver means along said curved member, said drive means further including resilient moving means for resiliently moving said pulser/receiver means along a path substantially perpendicular to said curved member and encouraging contact between said animal and said pulser/receiver means, and wherein said position signal is comprised of a displacement signal corresponding to the relative distance said pulser/receiver means is displaced from said predetermined path and a path signal corresponding to the relative location of said pulser/receiver means along said predetermined path defined by said curved member; and means for analyzing said ultrasound signals and said position signal to produce a leanness signal corresponding to lean content of the live animal or carcass wherein said means for analyzing includes a processor means having:
(1) means for digitizing and storing a plurality of corresponding ones of said ultrasound signal, said displacement signal and said path signal;
(2) means for determining muscle/fat tissue interface boundary locations in each of said ultrasound signals;
(3) means for calculating muscle tissue area from said muscle/tissue interface boundary locations and corresponding ones of said displacement signals and said path signals and thereby producing said leanness signal, wherein said muscle/fat tissue interface boundary locations in each ultrasound signal are determined by said processor means according to the following algorithm:
(1) dividing each digitized ultrasound signal into a predetermined quantity of data points;
(2) computing a mean value for each of said groups of data points;
(3) determining a muscle tissue entry time by analyzing the first half of said means values to ascertain the latest occurrence of one of said means values having a value in excess of a first predetermined peak limit; and
(4) determining a muscle tissue exit time by analyzing the second half of said means values to ascertain the latest occurrence of one of said mean values having a value in excess of a second predetermined peak limit.

21. The device of claim 20 wherein said predetermined path is a semi-circular arc.

22. The device of claim 21 wherein adjacent ones of said muscle tissue entry times and said muscle tissue exit times, in conjunction with corresponding ones of said displacement signal and said path signal, define unique quadrilaterals whose summed areas are the muscle area bounded thereby.

23. The device of claim 22 wherein said processor means includes a computer having ROM, RAM, analog I/O, serial I/O and parallel I/O, said computer receiving said displacement signal and said path signal from said drive means and said ultrasound signal from said ultrasonic pulser/receiver means, said computer also supplying a drive signal to said motor of said drive means thereby causing said motor to move said pulser/receiver means to one of a plurality of positions along said predetermined path defined by said curved member.

24. The device of claim 21 wherein said device is positioned adjacent the rib/loin area of the animal or carcass and wherein said motor moves said pulser/receiver means along said curved member and generally along the ribs of the animal while ultrasonically determining area of the longissimus muscle, and wherein the ventral longissimus muscle and the dorsal longissimus muscle areas are estimated.

25. The device of claim 24 including means for coupling said ultrasonic pulse signals to said animal or carcass, an encoder means attached to said motor and engaging said curved member to produce said path signal, and a linear displacement transducer means attached to said pulser/receiver means for producing said path signal.

26. The device of claim 25 wherein said means for coupling is a fluid manifold which defines a fluid reservoir surrounding said ultrasonic pulser/receiver means when said ultrasonic pulser/receiver means is urged in contact with said animal or carcass, and wherein ultrasonic coupling fluid is supplied to said fluid manifold to maintain coupling fluid between said animal or carcass and said ultrasonic pulser/receiver.

* * * * *